(12) United States Patent
Muller

(10) Patent No.: US 8,010,194 B2
(45) Date of Patent: Aug. 30, 2011

(54) DETERMINING SITE-TO-SITE PACING DELAY FOR MULTI-SITE ANTI-TACHYCARDIA PACING

(76) Inventor: David Muller, Sicklerville, NJ (US)

( * ) Notice: Subject to any disclaimer, the term of this patent is extended or adjusted under 35 U.S.C. 154(b) by 266 days.

(21) Appl. No.: 12/416,778

(22) Filed: Apr. 1, 2009

(65) Prior Publication Data

US 2010/0256701 A1    Oct. 7, 2010

(51) Int. Cl.
*A61N 1/00* (2006.01)
(52) U.S. Cl. .......................................... 607/14
(58) Field of Classification Search .................. 600/510; 607/14, 22, 9, 17
See application file for complete search history.

(56) References Cited

U.S. PATENT DOCUMENTS

| | | | |
|---|---|---|---|
| 4,712,555 A | 12/1987 | Thornander et al. | |
| 4,788,980 A | 12/1988 | Mann et al. | |
| 4,940,052 A | 7/1990 | Mann et al. | |
| 4,944,298 A | 7/1990 | Sholder | |
| 5,243,976 A * | 9/1993 | Ferek-Petric et al. | 607/6 |
| 5,330,507 A * | 7/1994 | Schwartz | 607/14 |
| 5,466,254 A | 11/1995 | Helland | |
| 6,512,952 B2 | 1/2003 | Stahmann et al. | |
| 6,628,988 B2 | 9/2003 | Kramer et al. | |
| 6,643,546 B2 | 11/2003 | Mathis et al. | |
| 7,236,821 B2 * | 6/2007 | Cates et al. | 607/2 |
| 2002/0183636 A1 * | 12/2002 | Struble | 600/510 |
| 2003/0055345 A1 | 3/2003 | Eigler et al. | |
| 2004/0215257 A1 | 10/2004 | Van Oort et al. | |
| 2008/0086177 A1 | 4/2008 | Min et al. | |
| 2008/0119903 A1 | 5/2008 | Arcot-Krishnamurthy et al. | |

FOREIGN PATENT DOCUMENTS

| | | |
|---|---|---|
| EP | 1911492 A1 | 5/2007 |
| WO | 2004096341 A2 | 11/2004 |

OTHER PUBLICATIONS

Right Ventricular Versus Biventricular Antitachycardia Pacing in the Termination of Ventricular Tachyarrhythmia in Patients Receiving Cardiac Resynchronization Therapy; The Advance CRT-D trial; J Cardiovasc Electrophysiol, vol. 17, pp. 504-507, May 2006.
BiV vs RV Pacing: Efficacy of First ATP Attempt in Terminating VT in Patients with CRT-D Devices; Gasparini M. Heart Rythm Society 2008 Scientific Sessions; May 15, 2008; San Francisco, CA.
Antitach-Pacing in CRT-Treated Heart Failure Explored in Randomized Study; HRS News, Jun. 6, 2008.

* cited by examiner

*Primary Examiner* — George Manuel
*Assistant Examiner* — Robert Wieland

(57) ABSTRACT

An exemplary method includes delivering a pace using an electrode positioned on the lateral wall of the left ventricle of a heart, sensing the pace using an electrode positioned in the right ventricle of the heart, determining a left to right directional conduction time ($T_{LR}$), delivering a pace using an electrode positioned in the right ventricle of the heart, sensing the pace using an electrode positioned on the lateral wall of the left ventricle of the heart, determining a right to left directional conduction time ($T_{RL}$), calculating a site-to-site offset ($VV_{ATP}$) for multi-site anti-tachycardia pacing based on the left to right directional conduction time and the right to left directional conduction time and instructing an implantable device to deliver multi-site anti-tachycardia pacing using the site-to-site offset ($VV_{ATP}$). Other exemplary methods, devices, systems, etc., are also disclosed.

18 Claims, 12 Drawing Sheets

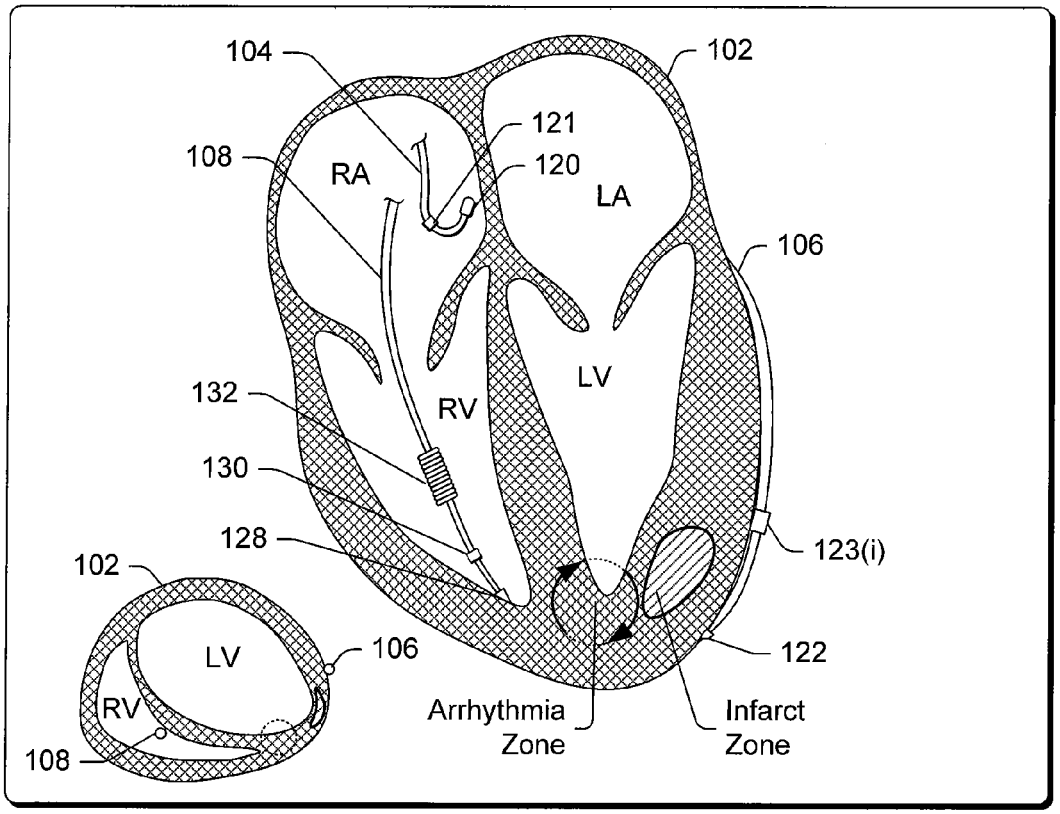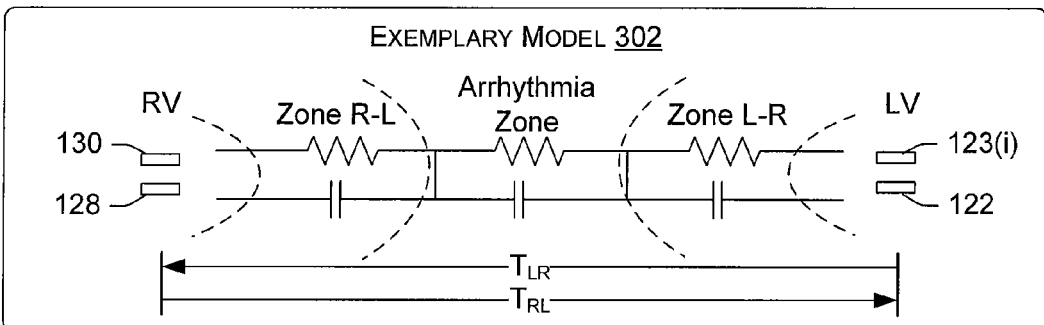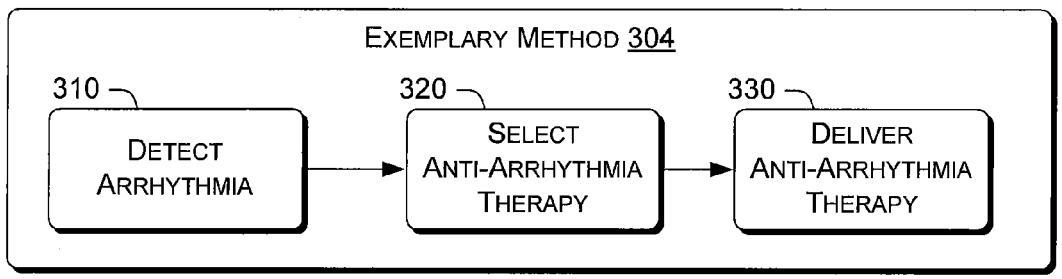
FIG. 3

TABLE 510: BiV vs RV PACING: EFFICACY OF FIRST ATP ATTEMPT IN TERMINATING VT IN PATIENTS WITH CRT-D DEVICES

| Type of VT | All patients (%) | BiV pacing (%) | RV pacing (%) | p |
|---|---|---|---|---|
| Any VT* | 66.5 | 64.7 | 68.2 | 0.588 |
| Fast VT | 65.5 | 71.2 | 61.1 | 0.335 |
| Slower VT | 66.0 | 61.6 | 70.5 | 0.24 |

TABLE 520: BiV vs RV PACING, BY HEART-FAILURE ETIOLOGY: EFFICACY OF FIRST ATP ATTEMPT IN TERMINATING VT IN PATIENTS WITH CRT-D DEVICES

| Etiology type of VT | BiV pacing (%) | RV pacing (%) | p |
|---|---|---|---|
| Any VT | | | |
|   Ischemic | 64.6 | 58.6 | 0.079 |
|   Nonischemic | 64.4 | 81.2 | 0.476 |
| Fast VT | | | |
|   Ischemic | 66.8 | 39.4 | 0.029 |
|   Nonischemic | 70.4 | 81.4 | 0.559 |

FIG. 5

DETERMINING SITE-TO-SITE PACING DELAY FOR MULTI-SITE ANTI-TACHYCARDIA PACING

TECHNICAL FIELD

Subject matter presented herein generally relates to anti-arrhythmia therapies, including anti-tachycardia pacing.

BACKGROUND

Various conditions can damage the myocardium and, in turn, such damage can alter electrical conduction of intrinsic and artificial myocardial stimuli. For example, ischemia can cause myocardial scarring that slows electrical conduction of a pacing stimulus or myocardial depolarization responsive to a pacing stimulus. Hence, after ischemia, a scar may delay depolarization of the myocardium responsive to a pacing stimulus. Ischemia and scaring can also lead to ventricular arrhythmias. For example, many ischemic cardiomyopathy patients experience left ventricle arrhythmias caused by altered zones of electrical conduction associated with injured tissue.

Anti-tachycardia pacing (ATP) has been utilized successfully to terminate ventricular arrhythmias in a great number of patients with ventricular tachycardia. ATP therapies work by disrupting wavefronts as they enter or exit these zones of altered conduction. An article by Schwab et al., "Right ventricular versus biventricular antitachycardia pacing in the termination of ventricular tachyarrhythmia in patients receiving cardiac resynchronization therapy" (J Cardiovasc Electrophysiol, Vol. 17, pp. 504-507, May 2006) proposed a study to assess differences between patients having implanted cardiac resynchronization therapy and defibrillation devices (CRT-D devices) programmed for right ventricular pacing and ATP or biventricular pacing and ATP. Some results for this study were reported by Gasparini ("Biventricular vs right ventricular antitachycardia pacing in the termination of ventricular tachyarrhythmia in patients receiving cardiac resynchronization therapy: The ADVANCE CRT-D trial. Heart Rhythm Society 2008 Scientific Sessions; May 15, 2008; San Francisco, Calif.). In a report of the results, it was stated (i) that arrhythmia symptoms (syncope or presyncope) during ATP of fast VT were more likely to develop with RV pacing, (ii) that "fast" VT might respond better to biventricular pacing while RV pacing may sometimes be best for slower VT episodes and (iii) that ATP with biventricular pacing appeared to be more effective in ischemic heart disease, with RV pacing performing better in nonischemic than ischemic patients (see, Stiles, "Antitach-pacing in CRT-treated heart failure explored in randomized study", HRS News, Jun. 6, 2008). These results demonstrate that risk of, and termination of, arrhythmias with respect to pacing regimen are only understood superficially.

As described herein, various exemplary techniques aim to treat arrhythmias by delivering stimulation energy via different stimulation sites. Such techniques may be applied to pacing regimens that rely on biventricular pacing (e.g., as implemented by CRT or CRT-D devices) or other pacing regimens that can delivery energy via two or more sites.

SUMMARY

An exemplary method includes delivering a pace using an electrode positioned on the lateral wall of the left ventricle of a heart, sensing the pace using an electrode positioned in the right ventricle of the heart, determining a left to right directional conduction time ($T_{LR}$), delivering a pace using an electrode positioned in the right ventricle of the heart, sensing the pace using an electrode positioned on the lateral wall of the left ventricle of the heart, determining a right to left directional conduction time ($T_{RL}$), calculating a site-to-site offset ($VV_{ATP}$) for multi-site anti-tachycardia pacing based on the left to right directional conduction time and the right to left directional conduction time and instructing an implantable device to deliver multi-site anti-tachycardia pacing using the site-to-site offset ($VV_{ATP}$). Other exemplary methods, devices, systems, etc., are also disclosed.

In general, the various methods, devices, systems, etc., described herein, and equivalents thereof, are optionally suitable for use in a variety of pacing therapies and other cardiac related therapies.

BRIEF DESCRIPTION OF THE DRAWINGS

Features and advantages of the described implementations can be more readily understood by reference to the following description taken in conjunction with the accompanying drawings.

FIG. 3 is a diagram of a heart showing an infarct zone and an arrhythmic zone, an electrical conduction model and an exemplary method for delivering anti-arrhythmia therapy.

FIG. 5 is a presentation of data in two tables where the data associates ventricular tachycardia type, ischemia and efficacy of a first anti-tachycardia pacing attempt at terminating ventricular tachycardia.

DETAILED DESCRIPTION

Figure 1:
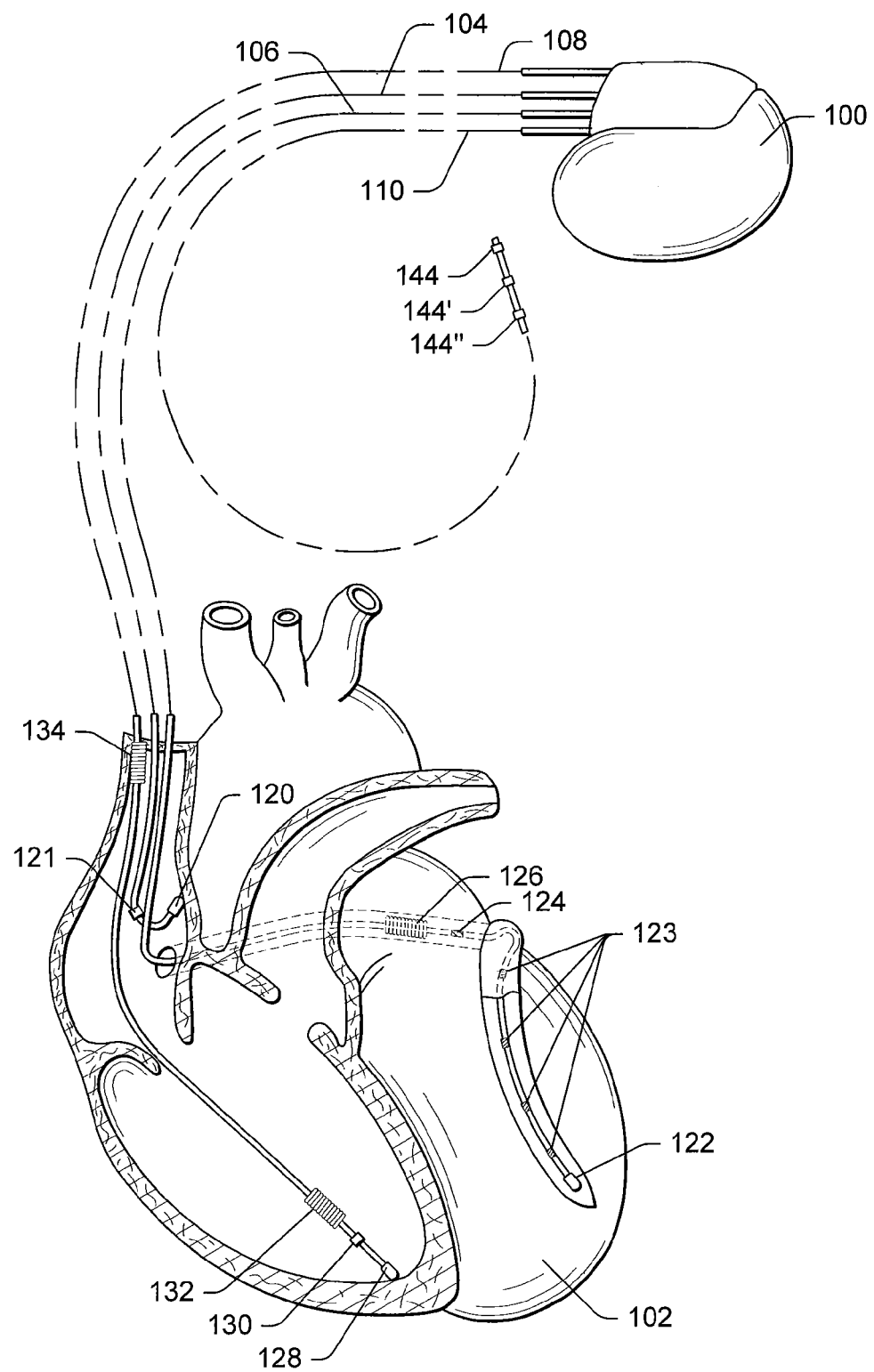
FIG. 1 is a simplified diagram illustrating an exemplary implantable stimulation device in electrical communication with three leads implanted into a patient's heart and another lead; other examples may have different lead arrangements (e.g., different number, placement, type, etc.).

The following description includes the best mode presently contemplated for practicing the described implementations.

This description is not to be taken in a limiting sense, but rather is made merely for the purpose of describing the general principles of the implementations. The scope of the described implementations should be ascertained with reference to the issued claims.

Overview

Most ventricular arrhythmias in ischemic cardiomyopathy patients occur in the left ventricle and are caused by altered zones of conduction within injured tissue. Anti-tachycardia pacing (ATP) has been utilized successfully to terminate ventricular arrhythmias in a large population of patients with ventricular tachycardia (VT). ATP therapies generate wavefronts that act to disrupt or confound arrhythmic activity. For example, ATP can disrupt arrhythmic wavefronts entering or exiting zones of altered conduction.

Various exemplary methods described herein call for and deliver anti-arrhythmia therapy (AAT), optionally including ATP. In some instances, AAT is delivered using multiple pacing sites where a time delay between two sites is determined based on directional conduction characteristics of the heart. For example, an exemplary method determines a conduction time for conduction in a first direction between two sites and a conduction time for conduction in a second direction between the two sites. When an arrhythmia is detected, AAT delivers energy via both sites according to a site-to-site (SS) delay based on the difference between the two conduction times for the sites. Such an approach aims to depolarize a large portion of the ventricles, which, in turn, increases the probability of terminating the arrhythmia (e.g., by interrupting its arrhythmic circuit). In other words, as multi-directional ATP wavefronts collide, the chance of the arrhythmia being terminated increases as more of the ventricular mass is depolarized.

With the use of cardiac resynchronization therapy and defibrillation devices (CRT-D devices), it is possible to brady pace the left ventricle via a lead placed in the coronary sinus. If a lead is present in the right ventricle and another lead is present on the left side of the heart, a CRT device can deliver ATP therapies in a biventricular, multi-site manner. In a biventricular approach to ATP, the area of pacing can be divided into three distinct zones of conduction spanning the two biventricular delivery sites. For most patients, ventricular conduction velocity remains relatively constant for some period of time (e.g., days or weeks). An exemplary algorithm includes determining (or estimating) conduction times through the aforementioned zones, based on acquired information, and then using the times to determine an optimal VV delay or offset to disrupt a re-entrant rhythm (e.g., delivering an ATP therapy that includes pacing an RV site prior to an LV site or vice versa according to the VV delay). In general, energy is delivered at a site corresponding to a longer directional conduction time and then energy is delivered at a site corresponding to a shorter directional conduction time according to the calculated delay.

Various exemplary techniques can be implemented within a broader context of anti-arrhythmia therapy. For example, as explained below, arrhythmias may be characterized (e.g., classified, located, etc.) and myocardial health may be assessed locally (e.g., healthy, ischemic, scarred, etc.). As to myocardial health, such assessments may be made by an implantable device, via imaging modalities, an external device, etc. Where an implantable device has knowledge of myocardial health in relationship to an arrhythmia (e.g., based on a model, acquired information, communicated information, etc.), control logic of the implantable device may select an appropriate anti-arrhythmia therapy based on the knowledge of myocardial health (e.g., multi-site AAT for termination of arrhythmias in ischemic regions).

Exemplary Stimulation Device

The techniques described below are optionally implemented in connection with a stimulation device that is configured or configurable to stimulate and/or shock tissue. With respect to assessment of cardiac condition (e.g., ischemia, arrhythmia, etc.), an implantable device may provide for acquiring information and analyzing information to assess cardiac condition even in the instance that the device does not provide for (or is not configured or programmed for) delivery of stimulation therapy.

FIG. 1 shows an exemplary stimulation device 100 in electrical communication with a patient's heart 102 by way of three leads 104, 106, 108, suitable for delivering multi-chamber cardiac stimulation and shock therapy. The leads 104, 106, 108 are optionally configurable for delivery of stimulation pulses suitable for stimulation of autonomic nerves, non-myocardial tissue, other nerves, etc. In addition, the device 100 includes a fourth lead 110 having, in this implementation, three electrodes 144, 144', 144" suitable for stimulation of any of a variety of tissues (e.g., myocardial, autonomic nerves, non-myocardial tissue, other nerves, etc.). For example, this lead may be positioned in and/or near a patient's heart or near an autonomic nerve within a patient's body and remote from the heart. Such a lead may also include one or more electrodes for epicardial placement (e.g., consider patch, screw, and other attachment mechanisms).

The right atrial lead 104, as the name implies, is positioned in and/or passes through a patient's right atrium. The right atrial lead 104 optionally senses atrial cardiac signals and/or provides for right atrial chamber stimulation therapy. The right atrial lead 104 may be used in conjunction with one or more other leads and/or electrodes to acquire cardiac electrograms and/or to delivery energy to the heart or other tissue. As shown in FIG. 1, the stimulation device 100 is coupled to an implantable right atrial lead 104 having, for example, an atrial tip electrode 120, which typically is implanted in the patient's right atrial appendage. The lead 104, as shown in FIG. 1, also includes an atrial ring electrode 121. Of course, the lead 104 may have other electrodes as well. For example, the right atrial lead optionally includes a distal bifurcation having electrodes suitable for use in stimulation of tissue.

To sense atrial cardiac signals, ventricular cardiac signals and/or to provide chamber pacing therapy, particularly on the left side of a patient's heart, the stimulation device 100 is coupled to a coronary sinus lead 106 designed for placement in the coronary sinus and/or tributary veins of the coronary sinus. Thus, the coronary sinus lead 106 is optionally suitable for positioning at least one distal electrode adjacent to the left ventricle and/or additional electrode(s) adjacent to the left atrium. In a normal heart, tributary veins of the coronary sinus include, but may not be limited to, the great cardiac vein, the left marginal vein, the left posterior ventricular vein, the middle cardiac vein, and the small cardiac vein.

In the example of FIG. 1, the coronary sinus lead 106 includes a series of electrodes 123. In particular, a series of four electrodes are shown positioned in an anterior vein of the heart 102 (e.g., traversing the lateral wall of the left ventricle). Other coronary sinus leads may include a different number of electrodes than the lead 106. As described herein, an exemplary method selects one or more electrodes (e.g., from electrodes 123 of the lead 106) and determines characteristics associated with conduction and/or timing in the heart to aid in ventricular pacing therapy, anti-arrhythmia therapy (ATT) and/or assessment of cardiac condition. In various instances, acquired information may be used to determine a suitable electrode configuration for the lead 106 (e.g., selection of one or more electrodes 123 of the lead 106).

An exemplary coronary sinus lead 106 can be designed to receive ventricular cardiac signals (and optionally atrial signals) and to deliver left ventricular pacing therapy using, for example, at least one of the electrodes 123 and/or the tip electrode 122. The lead 106 optionally allows for left atrial pacing therapy, for example, using at least the left atrial ring electrode 124. The lead 106 optionally allows for shocking therapy, for example, using at least the left atrial coil electrode 126. For a complete description of a coronary sinus lead, the reader is directed to U.S. Pat. No. 5,466,254, "Coronary Sinus Lead with Atrial Sensing Capability" (Helland), which is incorporated herein by reference.

The coronary sinus lead 106 further optionally includes electrodes for stimulation of other tissue. Such a lead may include pacing and autonomic nerve stimulation functionality and may further include bifurcations or legs. For example, an exemplary coronary sinus lead includes pacing electrodes capable of delivering pacing pulses to a patient's left ventricle and at least one electrode capable of stimulating an autonomic nerve. An exemplary coronary sinus lead (or left ventricular lead or left atrial lead) may also include at least one electrode capable of stimulating an autonomic nerve, non-myocardial tissue, other nerves, etc., wherein such an electrode may be positioned on the lead or a bifurcation or leg of the lead.

Stimulation device 100 is also shown in electrical communication with the patient's heart 102 by way of an implantable right ventricular lead 108 having, in this exemplary implementation, a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex or the RV outflow tract (RVOT) so that the RV coil electrode 132 will be positioned in the right ventricle and the SVC coil electrode 134 will be positioned in the superior vena cava. Accordingly, the right ventricular lead 108 is capable of sensing or receiving cardiac signals, and delivering stimulation in the form of pacing and shock therapy to the right ventricle. An exemplary right ventricular lead may also include at least one electrode capable of stimulating an autonomic nerve, non-myocardial tissue, other nerves, etc., wherein such an electrode may be positioned on the lead or a bifurcation or leg of the lead. A right ventricular lead may include a series of electrodes, such as the series 123 of the left ventricular lead 106.

Figure 2:
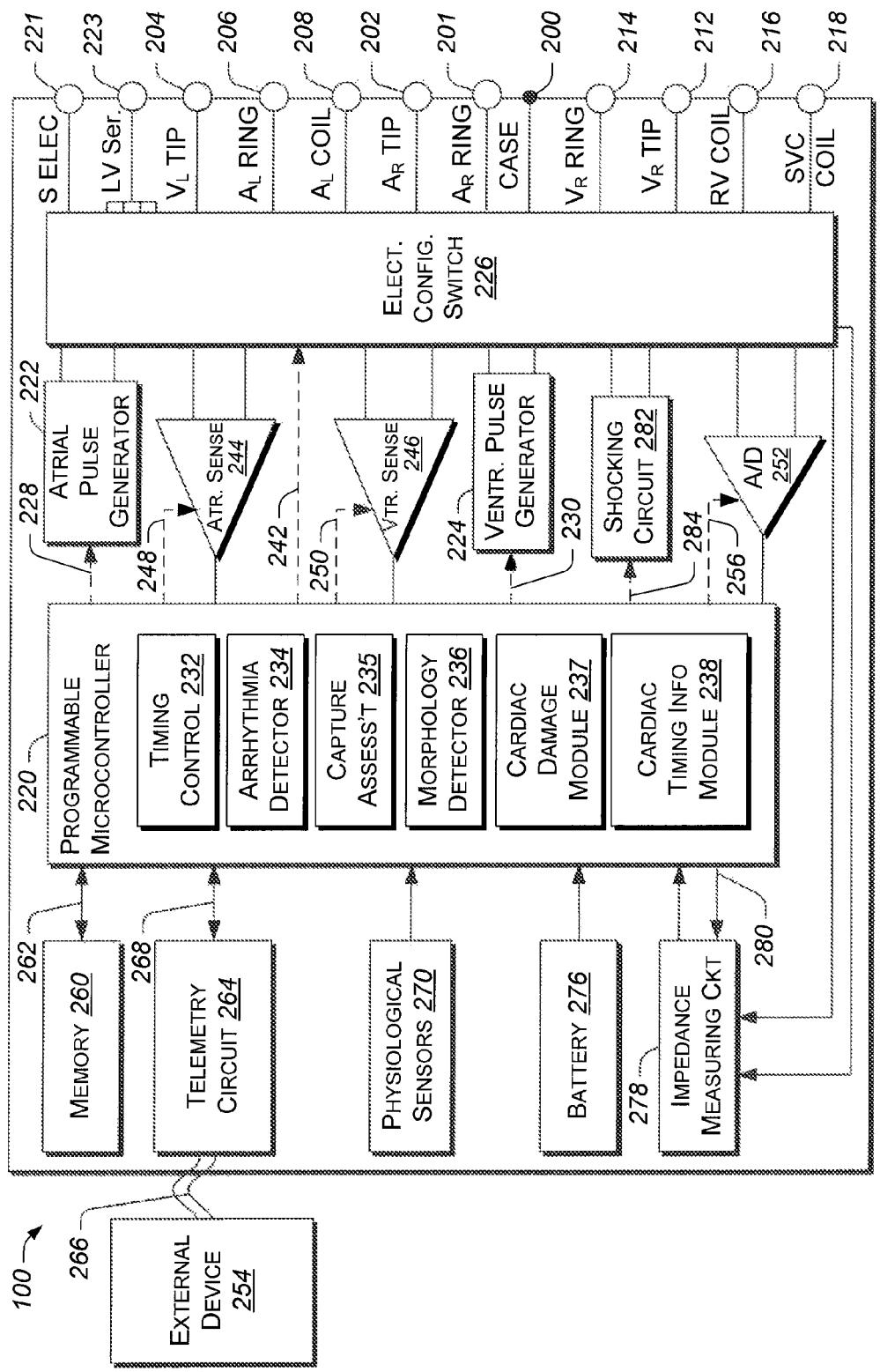
FIG. 2 is a functional block diagram of an exemplary implantable stimulation device illustrating basic elements that are configured to provide cardioversion, defibrillation, pacing stimulation and/or other functions. The implantable stimulation device is further configured to sense information and administer stimulation pulses responsive to such information.

FIG. 2 shows an exemplary, simplified block diagram depicting various components of stimulation device 100. The stimulation device 100 can be capable of treating both fast and slow arrhythmias with stimulation therapy, including cardioversion, defibrillation, and pacing stimulation. Various exemplary methods described in more detail below include detecting an arrhythmia and delivering anti-arrhythmia therapy. Such methods may deliver anti-arrhythmia therapy using one or more leads, for example, to approach arrhythmic tissue from more than one direction (e.g., vector).

The stimulation device of FIGS. 1 and 2 can capable of delivering stimuli to autonomic nerves, non-myocardial tissue, other nerves, etc. While a particular multi-chamber device is shown, it is to be appreciated and understood that this is done for illustration purposes only. Thus, the techniques and methods described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) or regions of a patient's heart with cardioversion, defibrillation, pacing stimulation, autonomic nerve stimulation, non-myocardial tissue stimulation, other nerve stimulation, etc. For purposes of assessment of cardiac condition, an exemplary implantable device may provide for acquiring information and analyzing such information without delivering stimulation therapy.

Housing 200 for stimulation device 100 is often referred to as the "can", "case" or "case electrode", and may be programmably selected to act as the return electrode for all "unipolar" modes. Housing 200 may further be used as an electrode alone or in combination with one or more of the coil electrodes 126, 132 and 134 for shocking purposes. In general, housing 200 may be used as an electrode in any of a variety of electrode configurations. Housing 200 further includes a connector (not shown) having a plurality of terminals 201, 202, 204, 206, 208, 212, 214, 216, 218, 221, 223 (shown schematically and, for convenience, the names of the electrodes to which they are connected are shown next to the terminals).

To achieve right atrial sensing, pacing, autonomic stimulation, etc., the connector includes at least a right atrial tip terminal ($A_R$ TIP) 202 adapted for connection to the atrial tip electrode 120. A right atrial ring terminal ($A_R$ RING) 201 is also shown, which is adapted for connection to the atrial ring electrode 121.

To achieve left chamber sensing, pacing, shocking, autonomic stimulation, etc., the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular tip electrode 122, the left atrial ring electrode 124, and the left atrial coil electrode 126, respectively.

A terminal 223 allows for connection of a series of left ventricular electrodes. For example, the series of four electrodes 123 of the lead 106 may connect to the device 100 via the terminal 223. The terminal 223 and an electrode configuration switch 226 allow for selection of one or more of the series of electrodes and hence electrode configuration. In the example of FIG. 2, the terminal 223 includes four branches to the switch 226 where each branch corresponds to one of the four electrodes 123.

Connection to suitable autonomic nerve stimulation electrodes or other tissue is also possible via aforementioned terminals and/or other terminals (e.g., via a stimulation terminal S ELEC 221).

To support right chamber sensing, pacing, shocking, autonomic nerve stimulation, etc., the connector further includes a right ventricular tip terminal ($V_R$ TIP) 212, a right ventricular ring terminal ($V_R$ RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively. Connection to suitable autonomic nerve stimulation electrodes is also possible via these and/or other terminals (e.g., via the stimulation terminal S ELEC 221).

At the core of the stimulation device 100 is a programmable microcontroller 220 that controls the various modes of stimulation therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller 220 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. No. 4,712,555 (Thornander et al.) and U.S. Pat. No. 4,944,298 (Sholder), all of which are incorporated by reference herein. For a more detailed description of the various timing intervals used within the stimulation device and their inter-relationship, see U.S. Pat. No. 4,788,980 (Mann et al.), also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via the electrode configuration switch 226. One or both of the generators 222 and 224 may optionally provide energy for delivery by the lead 110. It is understood that in order to provide stimulation therapy in each of the four chambers of the heart (or to autonomic nerves or other tissue) the atrial and ventricular pulse generators 222 and 224 may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate (A-to-A or V-to-V), atrio-ventricular (AV) delay, interatrial (AA) delay, or interventricular (VV) delay, etc.) as well as to keep track of the timing of refractory periods, blanking intervals, noise detection windows, evoked response windows, alert intervals, marker channel timing, etc., which is well known in the art.

Microcontroller 220 further includes an arrhythmia detector 234, a capture assessment module 235, a morphology detector 236, and optionally an orthostatic compensator and a minute ventilation (MV) response module, the latter two are not shown in FIG. 2. The components can be utilized by the stimulation device 100 for determining desirable times to administer various therapies and for determining appropriate energy levels for delivery of stimuli to the heart. The aforementioned components may be implemented in hardware as part of the microcontroller 220, or as software/firmware instructions programmed into the device and executed on the microcontroller 220 during certain modes of operation.

Microcontroller 220 further includes a cardiac damage module 237 for analyzing information to determine whether damage exists and/or to determine location of one or more cardiac regions or zones, for example, as related to cardiac damage and/or health (e.g., blood flow/ischemia or other). The module 237 may use information acquired via one or more of the physiological sensors 270, information acquired via a lead (consider, e.g., leads 104, 106, 108, 110), and/or information acquired via the telemetry circuit 264 (e.g., from an external device). The module 237 may receive information from one or more modules and/or transmit information to one or more modules. The module 237 may act to control various features of the device 100 (e.g., timing of stimulation, timing of sensing, etc.). Module 237 may be implemented in hardware as part of the microcontroller 220, or as software/firmware instructions programmed into the device and executed on the microcontroller 220 during certain modes of operation.

Microcontroller 220 further includes a cardiac timing information module 238 for determining one or more cardiac timing parameters. The module 238 may include logic to determine an intrinsic conduction delay between right ventricular activation and left ventricular activation, an interval between stimulation of one ventricle and sensing of propagated electrical activity to the other ventricle, etc. The module 238 may include logic for determining one or more parameters for an anti-arrhythmia therapy or therapies. For example, the arrhythmia detection module 234 may detect an arrhythmia and the timing module 238 may determine timing for delivery of an anti-arrhythmia therapy.

The module 238 may be implemented in hardware as part of the microcontroller 220, or as software/firmware instructions programmed into the device and executed on the microcontroller 220 during certain modes of operation. The module 238 may operate based in part on analyses performed using the module 237. Further, while the modules are shown as individual modules, other arrangements are possible. The module 238 may operate based in part on information acquired using a capture algorithm or, more generally, a capture assessment method (e.g., per the module 235).

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, combipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, the right ventricular lead 108 and/or the lead 110 through the switch 226 for detecting the presence of cardiac activity in each of the four chambers of the heart. Accordingly, the atrial (ATR. SENSE) and ventricular (VTR. SENSE) sensing circuits 244 and 246 may include dedicated sense amplifiers, multiplexed amplifiers or shared amplifiers. Switch 226 can determine the "sensing polarity" of the cardiac signal by selectively closing the appropriate switches, as is also known in the art. In this way, a clinician may program the sensing polarity independent of the stimulation polarity. An exemplary method may optionally control polarity. For example, the module 237 may include control logic to select an electrode configuration with a particular polarity. The sensing circuits (e.g., 244 and 246) are optionally capable of obtaining information indicative of tissue capture for use by the capture assessment module 235. As described further below, capture information may be used to assess cardiac condition and/or to optimize delivery of a stimulation therapy.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or an data acquisition system 252 to determine or detect whether and to what degree tissue capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits 244 and 246, as is known in the art.

Information acquired by any of the sensing circuits (e.g., 244, 246, 252) is optionally used in a control scheme implemented at least in part by the microcontroller 220. For example, the module 237 may use cardiac electrograms acquired via the ventricular sensing circuitry 246 in an analysis that aims to determine location of one or more cardiac regions or zones. In turn, such an analysis may be used by the module 238 to determine timing for delivery of a pacing pulse or pulses.

For arrhythmia detection, the device 100 utilizes the atrial and ventricular sensing circuits 244 and 246 to sense cardiac signals to determine whether a rhythm is physiologic or pathologic. In reference to arrhythmias, as used herein, "sensing" is reserved for the noting of an electrical signal or obtaining data (information), and "detection" is the processing (analysis) of these sensed signals or obtained information and noting the presence of an arrhythmia. In some instances, detection or detecting includes sensing and in some instances sensing of a particular signal alone is sufficient for detection (e.g., presence/absence, etc.).

The timing intervals between sensed events (e.g., P-waves, R-waves, and depolarization signals associated with fibrillation) are then classified by the arrhythmia detector 234 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to inputs of the analog-to-digital (A/D) data acquisition system 252. The data acquisition system 252 is configured to acquire cardiac electrogram signals (e.g., intracardiac electrograms or other), convert the raw analog data into a digital signal, and store the digital signals for later processing and/or telemetric transmission to an external device 254. A signal line 256 allows for control of the data acquisition system 252 (e.g., via programmed logic of the microcontroller 220). The data acquisition system 252 is coupled to the right atrial lead 104, the coronary sinus lead 106, the right ventricular lead 108 and/or the lead 110 through the switch 226 to sample cardiac signals or other signals (e.g., nerves, etc.) across any pair of desired electrodes.

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape, number of pulses, and vector of each shocking pulse to be delivered to the patient's heart 102 within each respective tier of therapy. The exemplary device 100 typically includes capabilities to acquire (e.g., sense or otherwise receive) and store a relatively large amount of data (e.g., from the atrial sensing circuitry 244, the ventricular sensing circuitry 246, data acquisition system 252, the one or more physiological sensors 270, the telemetry circuit 264), which data may then be used for subsequent analysis to guide operation of the device 100.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms and status information relating to the operation of the device 100 (as contained in the microcontroller 220 or memory 260) to be sent to the external device 254 through an established communication link 266.

The stimulation device 100 can further include one or more physiological sensors 270. For example, the device 100 may include a rate-responsive sensor for use in adjusting a pacing stimulation rate according to a sensed activity state (e.g., rest, exercise, etc.) of a patient. The one or more physiological sensors 270 may be capable of acquiring information for use in detecting changes in cardiac output (see, e.g., U.S. Pat. No. 6,314,323, entitled "Heart stimulator determining cardiac output, by measuring the systolic pressure, for controlling the stimulation" (Ekwall), which discusses a pressure sensor adapted to sense pressure in a right ventricle and to generate an electrical pressure signal corresponding to the sensed pressure, an integrator supplied with the pressure signal which integrates the pressure signal between a start time and a stop time to produce an integration result that corresponds to cardiac output), detecting changes in the physiological condition of the heart, detecting diurnal changes in activity (e.g., detecting sleep and wake states), etc. Accordingly, the microcontroller 220 may respond by adjusting any of the various pacing parameters (such as rate, AA delay, AV delay, VV delay, etc.) at which the atrial and ventricular pulse generators, 222 and 224, generate stimulation pulses. As already mentioned, a device may acquire information and then use the information to assess cardiac condition, regardless of whether the device is configured or programmed to deliver a stimulation therapy.

While shown as being included within the stimulation device 100, it is to be understood that any of the one or more physiological sensors 270 may also be external to the stimulation device 100, yet implanted within or carried by a patient. Examples of physiological sensors that may be implemented in device 100 include known sensors that, for example, sense respiration rate, pH of blood, ventricular gradient, cardiac output, preload, afterload, contractility, hemodynamics, pressure, and so forth. Another sensor that may be used is one that detects activity variance, wherein an activity sensor is monitored diurnally to detect the low variance in the measurement corresponding to the sleep state. For a complete description of the activity variance sensor, the reader is directed to U.S. Pat. No. 5,476,483 (Bornzin et al.), which patent is hereby incorporated by reference.

The one or more physiological sensors 270 optionally include sensors for detecting movement and minute ventilation in the patient. The one or more physiological sensors 270 may include a position sensor and/or a minute ventilation (MV) sensor to sense minute ventilation, which is defined as the total volume of air that moves in and out of a patient's lungs in a minute. Signals generated by the position sensor and MV sensor can be passed to the microcontroller 220 for analysis in determining whether to adjust the pacing rate, etc. The microcontroller 220 monitors the signals for indications of the patient's position and activity status, such as whether the patient is climbing upstairs or descending downstairs or whether the patient is sitting up after lying down.

The one or more physiological sensors 270 may include a pressure sensor. Pressure sensors for sensing left atrial pressure are discussed in U.S. Patent Application US2003/0055345 A1 (Eigler et al.), which is incorporated by reference herein. The discussion pertains to a pressure transducer permanently implantable within the left atrium of the patient's heart and operable to generate electrical signals indicative of fluid pressures within the patient's left atrium. According to Eigler et al., the pressure transducer is connected to a flexible electrical lead, which is connected in turn to electrical circuitry, which includes digital circuitry for processing electrical signals. Noted positions of the transducer include within the left atrium, within a pulmonary vein, within the left atrial appendage and in the septal wall.

The exemplary device 100 optionally includes a connector capable of connecting a lead that includes a pressure sensor. For example, the connector 221 optionally connects to a pressure sensor capable of receiving information pertaining to chamber pressures or other pressures.

The one or more physiological sensors 270 optionally include an oxygen sensor. The companies Nellcor (Pleasanton, Calif.) and Masimo Corporation (Irvine, Calif.) market pulse oximeters that may be used externally (e.g., finger, toe, etc.). Where desired, information from such external sensors may be communicated wirelessly to the implantable device using appropriate circuitry such as that found in a programmer for an implantable device (see, e.g., the programmer 1280 of FIG. 12).

The exemplary device 100 optionally includes a connector capable of connecting a lead that includes a sensor for sensing oxygen information. For example, the connector 221 optionally connects to a sensor for sensing information related blood oxygen concentration. Such information is optionally processed or analyzed by any of the various modules.

The stimulation device 100 optionally includes circuitry capable of sensing heart sounds and/or vibration associated with events that produce heart sounds. Such circuitry may include an accelerometer as conventionally used for patient position and/or activity determinations. Accelerometers typically include two or three sensors aligned along orthogonal axes. For example, a commercially available micro-electromechanical system (MEMS) marketed as the ADXL330 by Analog Devices, Inc. (Norwood, Mass.), is a small, thin, low power, complete three axis accelerometer with signal conditioned voltage outputs, all on a single monolithic IC. The ADXL330 product measures acceleration with a minimum full-scale range of ±3 g. It can measure the static acceleration of gravity in tilt-sensing applications, as well as dynamic acceleration resulting from motion, shock, or vibration. Bandwidths can be selected to suit the application, with a range of 0.5 Hz to 1,600 Hz for X and Y axes, and a range of 0.5 Hz to 550 Hz for the Z axis. Various heart sounds include frequency components lying in these ranges. The ADXL330 is available in a small, low-profile, 4 mm×4 mm×1.45 mm, 16-lead, plastic lead frame chip scale package (LFCSP_LQ).

While an accelerometer may be included in the case of an implantable pulse generator device, alternatively, an accelerometer communicates with such a device via a lead or through electrical signals conducted by body tissue and/or fluid. In the latter instance, the accelerometer may be positioned to advantageously sense vibrations associated with cardiac events. For example, an epicardial accelerometer may have improved signal to noise for cardiac events compared to an accelerometer housed in a case of an implanted pulse generator device.

As described herein, ischemia, injury and/or infarct may be detectable by various changes in physiology and hence by any of a variety of physiologic sensors, which can include use of aforementioned leads 104, 106, 108, 110 as electrical activity sensors. Ischemia, injury and/or infarct may be detectable based on temperature changes, decreased local myocardial pressure, decreased myocardial pH, decreased myocardial $pO_2$, increased myocardial $pCO_2$, increased myocardial lactate, increased ratio of lactate to pyruvate in the myocardium, increased ratio of the reduced form of nicotine amide adenine dinucleotide (NADH) to nicotine amide adenine dinucleotide ($NAD^+$) in the myocardium, increased ratio of the reduced form of nicotinamine-adenine dinucleotide phosphate (NADPH) to nicotinamine-adenine dinucleotide phosphate (NADPH) in the myocardium, increased ST segment, decreased ST segment, ventricular tachycardia, T wave changes, QRS changes, decreased patient activity, increased respiratory rate, decreased transthoracic impedance, decreased cardiac output, increased pulmonary artery diastolic pressure, increased myocardial creatinine kinase, increased troponin, and changed myocardial wall motion. Sensed information pertaining to ischemia, injury and/or infarct as well as exemplary mechanisms for sensing such information is discussed in more detail below.

The stimulation device additionally includes a battery 276 that provides operating power to all of the circuits shown in FIG. 2. For the stimulation device 100, which employs shocking therapy, the battery 276 is capable of operating at low current drains for long periods of time (e.g., preferably less than 10 μA), and is capable of providing high-current pulses (for capacitor charging) when the patient requires a shock pulse (e.g., preferably, in excess of 2 A, at voltages above 2 V, for periods of 10 seconds or more). The battery 276 also desirably has a predictable discharge characteristic so that elective replacement time can be detected.

The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds, edema, heart failure or other indicators; detecting when the device has been implanted; measuring stroke volume; and detecting the opening of heart valves; etc. The impedance measuring circuit 278 is advantageously coupled to the switch 226 so that any desired electrode may be used.

In the case where the stimulation device 100 is intended to operate as an implantable cardioverter/defibrillator (ICD) device, it can detect the occurrence of an arrhythmia and apply an appropriate therapy to the heart aimed at terminating the detected arrhythmia. To this end, the microcontroller 220 further controls a shocking circuit 282 by way of a control signal 284. The shocking circuit 282 generates shocking pulses of low (e.g., up to approximately 0.5 J), moderate (e.g., approximately 0.5 J to approximately 10 J), or high energy (e.g., approximately 11 J to approximately 40 J), as controlled by the microcontroller 220. Such shocking pulses may be applied to the patient's heart 102 through at two or more shocking electrodes (consider, e.g., the left atrial coil electrode 126, the RV coil electrode 132, and/or the SVC coil electrode 134). As noted above, the housing 200 may act as an active electrode in combination with the RV electrode 132, or as part of a split electrical vector using the SVC coil electrode 134 or the left atrial coil electrode 126 (i.e., using the RV electrode as a common electrode). Other exemplary devices may include one or more other coil electrodes or suitable shock electrodes (e.g., a LV coil, etc.).

Cardioversion level shocks are generally considered to be of low to moderate energy level (where possible, so as to minimize pain felt by the patient), and/or synchronized with an R-wave and/or pertaining to the treatment of tachycardia. Defibrillation shocks are generally of moderate to high energy level (i.e., corresponding to thresholds in the range of approximately 5 J to approximately 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

The device 100 may be configured to delivery cardiac resynchronization therapy. In general, cardiac resynchronization therapy delivers stimulation to improve overall cardiac function. This may have the additional beneficial effect of reducing the susceptibility to life-threatening tachyarrhythmias. CRT and related therapies are discussed in, for example, U.S. Pat. No. 6,643,546 (Mathis et al.), entitled "Multi-Electrode Apparatus and Method for Treatment of Congestive Heart Failure"; U.S. Pat. No. 6,628,988 (Kramer et al.) entitled "Apparatus and Method for Reversal of Myocardial Remodeling with Electrical Stimulation"; and U.S. Pat. No. 6,512,952 (Stahmann et al.), entitled "Method and Apparatus for Maintaining Synchronized Pacing," which are incorporated by reference herein. An exemplary implantable CRT device optionally includes electrodes for epicardial placement. For example, the lead 110 may include one or more electrodes for epicardial placement.

Arrhythmias and Cardiac Damage

As described herein, arrhythmias may be possibly associated with cardiac damage or possibly not. Cardiac damage may be caused by any of a variety of factors such as congenital conditions, drugs, trauma, etc. A common cause of cardiac damage is atherosclerosis or clotting. For example, a partially occluded artery can cause insufficient supply of blood to the myocardium and result in myocardial ischemia, injury or infarction, or all three. Atherosclerosis of any of the larger coronary arteries is the most common anatomic condition to diminish coronary blood flow. Branches of coronary arteries arising from the aortic root are distributed on the epicardial surface of the heart. These in turn provide intramural branches that supply the cardiac muscle. Myocardial ischemia generally appears first and is more extensive in the sub-endocardial region since these deeper myocardial layers are farthest from the blood supply, with greater intramural tension and need for oxygen.

In the context of the device 100 of FIGS. 1 and 2, an electrode or sensor may be located at a site in a damaged region or zone (e.g., infarct zone), a site that neighbors or borders a damaged region or zone of the heart or in a site remote from a damaged region or zone. A bordering zone or border zone may be considered a margin adjacent damaged tissue where a potential for ischemic growth exists. For example, damaged tissue may cause harm neighboring tissue (e.g., chemical release, change in pH, further deterioration in blood flow, etc.). A border zone or margin may have a breadth of about a centimeter or a couple of centimeters from the outer extent of the damaged tissue. To locate damage, various techniques may be used, some of which are explained further below with respect to FIG. 6.

FIG. 3 shows a diagram of the heart 102 (in two cross-sectional views), an electrical circuit model 302 and an exemplary method 304. The cross-sectional views of the heart 102 show the leads 104, 106 and 108 of FIG. 1. Specifically, the right atrial lead 104 is shown with the tip electrode 120 and the ring electrode 121, the left ventricular lead 106 is shown with the tip electrode 122 and one of the series of electrodes 123(*i*) and the right ventricular lead 108 is shown with the tip electrode 128, the ring electrode 130 and the coil electrode 132.

Also shown in the cross-sectional views of the heart 102 are an infarct zone and an arrhythmic zone. In the example of FIG. 3, the infarct zone and the arrhythmic zone are located in myocardium between a first electrode pair (electrodes 128, 130) of the right ventricular lead 108 and a second electrode pair (electrodes 122, 123(*i*)) of the left ventricular lead 106. The electrical model 302 illustrates the arrhythmic zone as being bound by a right-to-left zone (Zone R-L) and a left-to-right zone (Zone L-R). According to the model 302, a wavefront emanating from the first pair of electrodes (electrodes 128, 130) traverses the Zone R-L and then the arrhythmic zone while a wavefront emanating from the second pair of electrodes (electrodes 122, 123(*i*)) traverses the Zone L-R and then the arrhythmic zone.

As indicated by a time line, the wavefront from the first pair of electrodes (electrodes 128, 130) can be sensed by the second pair of electrodes (electrodes 122, 123(*i*)) and assigned a travel time or conduction time of $T_{RL}$ while the wavefront from the second pair of electrodes (electrodes 122, 123(*i*)) can be sensed by the first pair of electrodes (electrodes 128, 130) and assigned a travel or conduction time of $T_{LR}$.

In the example of FIG. 3, the infarct zone alters the conduction properties between the second pair of electrodes (electrodes 122, 123(*i*)) and the arrhythmic zone. This may be accounted for in the electrical model 302 by the resistive and/or capacitive properties (e.g., dielectric properties) of the Zone L-R. A wavefront emanating from a pair of electrodes, especially where the spacing between the electrodes is not very large (e.g., less than a centimeter), propagates roughly spherically. Given such a conduction scenario, the conduction times $T_{LR}$ and $T_{RL}$ may differ. Various exemplary methods described herein can optionally rely on a difference in conduction times when selecting a type of anti-arrhythmia therapy or to set one or more parameters of an anti-arrhythmia therapy.

The exemplary method 304 of FIG. 3 includes a detection block 310 for detecting an arrhythmia, a selection block 320 for selecting an anti-arrhythmia therapy (e.g., including setting one or more parameters) and a delivery block 330 for delivering a selected anti-arrhythmia therapy.

As described in more detail below, the method 304 may account for any of a variety of factors, including the type of arrhythmia, condition of the heart and possible electrode configurations.

Figure 4:
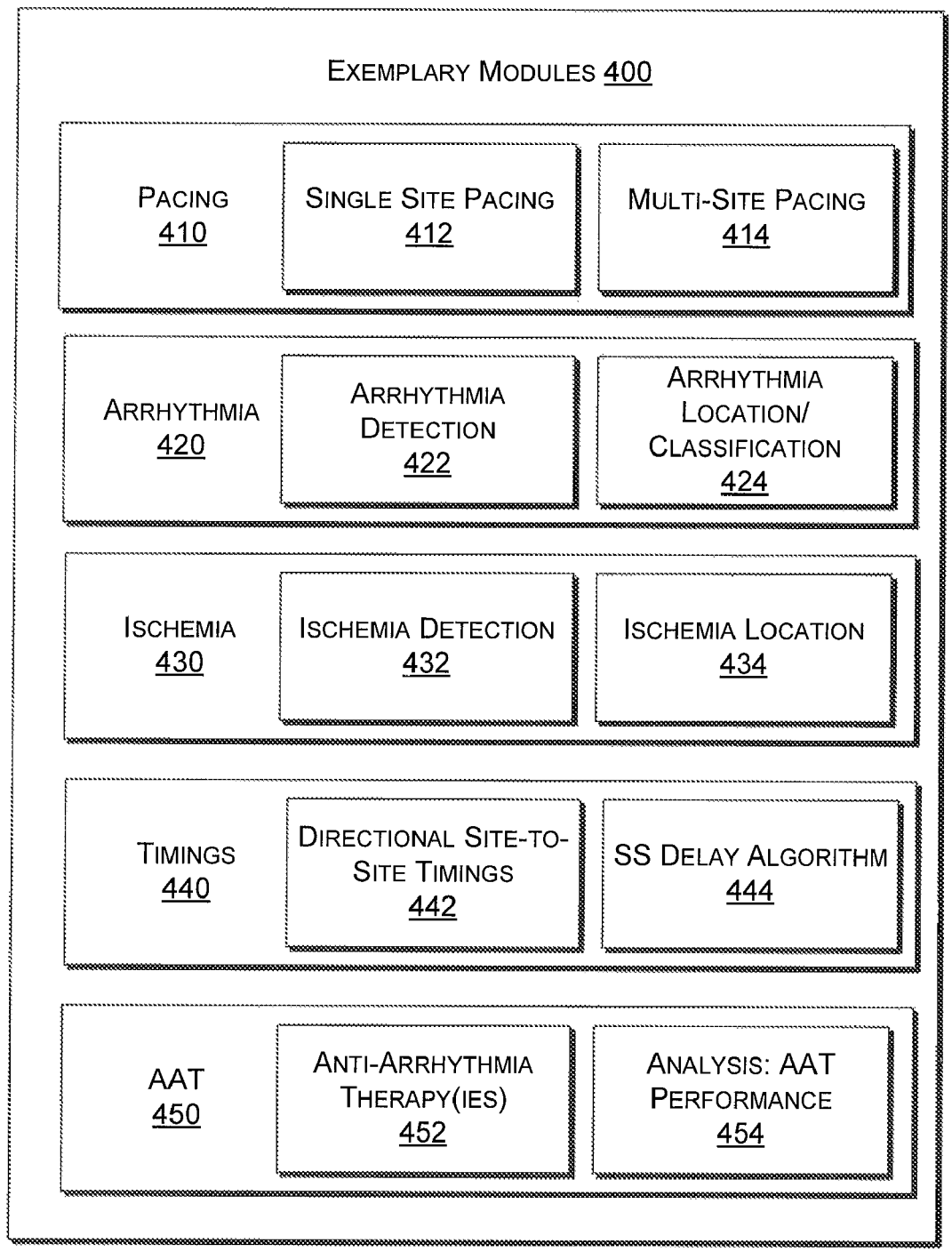
FIG. 4 is a diagram of exemplary modules for use in controlling an implantable device such as the device of FIGS. 1 and 2.

FIG. 4 shows exemplary modules 400 that may be implemented by the device 100 of FIG. 1. The modules 400 may be instructions executable using one or more processors and associated circuitry, for example, as described with respect to FIG. 2. Such instructions may be stored in memory and executed in response to control logic that may rely on sensing, detecting, communicating, etc. For example, instructions associated with a module may be executed upon receipt of a signal from an external device, upon detection of certain cardiac activity, upon an occurrence of a timed event (e.g., a scheduled event), etc.

The modules 400 include pacing modules 410, arrhythmia modules 420, ischemia modules 430 timings modules 440 and anti-arrhythmia modules 450. The modules 400 can operate in a cooperative manner to deliver pacing therapy (410), to detect arrhythmias (420), to detect and/or locate ischemia (430), to determine timings for delivery of stimulation to the heart (440), to deliver anti-arrhythmia therapy (440) and to analyze performance of anti-arrhythmia therapy (450).

The pacing modules 410 include a module 412 for single site pacing and a module 414 for multi-site pacing. For example, the modules 410 may call for delivery of energy to a right ventricular site, call for delivery of energy to a right ventricular site and a left ventricular site, call for delivery of energy to two right ventricular sites or call for delivery of energy to two left ventricular sites.

The arrhythmia modules 420 include a module 422 for detection of arrhythmias and a module 424 for location and/or classification of arrhythmias. For example, the arrhythmia modules 420 may receive sensed information and then, based on the sensed information, issue an alert indicating that an arrhythmia has been detected. The alert may further indicate type and/or location of the detected arrhythmia. The modules 420 may store information to allow for diagnosing patient condition (e.g., frequency of occurrence, type of arrhythmia, location of arrhythmia). Such information may assist a clinician in programming pacing therapy and/or anti-arrhythmia therapy. As discussed herein, a detection module may issue an alert or otherwise trigger an anti-arrhythmia therapy.

The ischemia modules 430 include an ischemia detection module 432 and an ischemia location module 434. The modules 432, 434 may rely on sensed information for detection and location of ischemia. For example, ischemia can cause chemical, mechanical, temperature and electrical changes to the heart. As described herein, a chemical sensor may sense chemical information, a mechanical sensor (e.g., an accelerometer, a strain gauge, etc.) may sense mechanical information, a temperature sensor (e.g., a thermocouple) may sense temperature information, one or more electrodes may sense electrical information.

The timings modules 440 include a direction site-to-site timings module 442 and a site-to-site (SS) delay algorithm for an anti-arrhythmia therapy 444 (e.g., anti-tachycardia pacing or other therapy). For example, where an anti-tachycardia pacing therapy relies on delivering energy via a right ventricular site and delivering energy via a left ventricular site, then the SS algorithm may determine a time delay that delays delivery of energy to the right ventricular site or that delays delivery of energy to the left ventricular site (e.g., a $VV_{ATP}$ delay).

The AAT modules 450 includes an anti-arrhythmia therapy (ies) module 452 and an analysis module 454. The anti-arrhythmia therapy(ies) module 452 may included therapies in a tiered structure where failure of a therapy at one tier calls for delivery of a therapy at another tier. The analysis module 452 may assess the success or failure of a therapy in terminating an arrhythmia, optionally with respect to delivery of one or more other therapies. Such an analysis may be part of a learning algorithm that aims to increase successful termination of arrhythmias. Such an analysis may further account for patient condition, activity state, etc. A patient may be provided a mechanism for feedback to minimize the use of a therapy or parameters that cause pain or discomfort.

FIG. 5 shows tables 510, 520 that include results as reported by Stiles, "Antitach-pacing in CRT-treated heart failure explored in randomized study", HRS News, Jun. 6, 2008 (citing Gasparini, "Biventricular vs right ventricular anti-tachycardia pacing in the termination of ventricular tachyarrhythmia in patients receiving cardiac resynchronization therapy: The ADVANCE CRT-D trial. Heart Rhythm Society 2008 Scientific Sessions; May 15, 2008; San Francisco, Calif.).

The results of table 510 and/or table 520 may be relied on for selecting an anti-arrhythmia therapy. With respect to the modules 400 of FIG. 4 and the implantable device 100 of FIGS. 1 and 2, such an implantable device may be programmed to deliver various anti-arrhythmia therapies and to analyze success and/or failure of these therapies to construct percentage or probability tables for use in selecting an anti-arrhythmia therapy that has an increased chance of success. As described herein, such an analysis can optionally note conditions associated with an arrhythmia (e.g., patient activity, type of pacing, ischemia, respiration rate, sleep apnea, base rate, etc.) and then associate an anti-arrhythmia therapy with certain conditions.

In the table 510, the results indicate that patients subject to biventricular pacing had an efficacy of 71.2% for a first ATP attempt in terminating fast VT while patients subject to RV pacing had an efficacy of only 61.1% (p=0.335). In contrast, patients subject to RV pacing had an efficacy of 70.5% for a first ATP attempt in terminating slow VT while patients subject to biventricular pacing had an efficacy of only 61.6% (p=0.24).

In the table 520, ischemic patients subject to biventricular pacing had an efficacy of 66.8% for a first ATP attempt in terminating fast VT while ischemic patients subject to RV pacing had an efficacy of only 39.4% (p=0.029). In contrast, nonischemic patients subject to RV pacing had an efficacy of 81.2% for a first ATP attempt in terminating "any type" of VT while ischemic patients subject to biventricular pacing had an efficacy of only 64.4% (p=0.476).

In the study, an implantable device detected VT when it sensed 20 consecutive intervals (12 for a redetection) to be $\leq 420$ ms ($\geq 143$ bpm). The device detected VF when it sensed that 18 of the most recent 24 intervals (9 out of 12 for redetection) were $\leq 240$ ms (>250 bpm). The device determined FVT based on the same detection criteria as VF (FVT via the VF zone) used in the PainFREE II trial. If any of the last 8 intervals were in the VF zone, i.e., <240 ms (>250 bpm), the arrhythmia was classified as VF, and the first programmed shock therapy was delivered. If all of the last 8 intervals were outside the VF zone, i.e., between 240 and 320 ms (250 to 188 bpm), the device detected the episode as FVT, and an ATP therapy was delivered.

In the study, the first VT and FVT therapy consisted of ATP with a burst of 8 pulses and a coupling interval of 88% of the preceding cycle length. Past successful implantation, optimization of the atrioventricular pacing delay, as well as the timing between RV and LV pacing were strongly recommended, but left to the physician's discretion.

In the study, site choice for delivery of ATP was randomized in an effort to meet the objective to compare the efficacy of RV versus BiV burst ATP therapies (8 pulses, 88% coupling interval) for the treatment of VT and FVT. Based on a prior study, for a group of 200 patients, it was expected that 104 patients would experience over 2000 FVT or VT episodes after 12 months of the follow-up period.

As mentioned, an implantable device may detect and/or locate ischemia and then use such information to select an anti-arrhythmia therapy. With respect to classification of damaged myocardial regions, the International Classification of Diseases, Clinical Modification (ICD-9-CM) has been used to code and classify morbidity data from the inpatient and outpatient records, physician offices, and most National Center for Health Statistics (NCHS) surveys. As described herein, a region, zone or border identified may be optionally classified using one or more of the ICD-9-CM diagnosis codes. For example, ICD-9-CM diagnosis codes include:

- 410.01 (anterolateral wall, acute myocardial infarction-initial episode),
- 410.11 (other anterior wall, acute myocardial infarction-initial episode),
- 410.21 (inferolateral wall, acute myocardial infarction-initial episode),
- 410.31 (inferoposterior wall, acute myocardial infarction-initial episode),
- 410.41 (other inferior wall, acute myocardial infarction-initial episode),
- 410.51 (other lateral wall, acute myocardial infarction-initial episode),
- 410.61 (true posterior wall, acute myocardial infarction-initial episode),
- 410.71 (subendocardial, acute myocardial infarction-initial episode),
- 410.81 (other specified sites, acute myocardial infarction-initial episode) and
- 410.91 (unspecified site, acute myocardial infarction-initial episode).

While various forms of information may be used to locate damage and/or neighboring tissue, various exemplary methods use cardiac electrograms. A cardiac electrogram may be acquired using electrodes implanted in the body (e.g., subcutaneous, intracardiac, etc.) and/or so-called surface electrodes (e.g., cutaneous electrodes, etc.). In general, a cardiac electrogram acquired using one or more of the former types of electrodes is labeled an EGM while a cardiac electrogram acquired using solely the latter type of electrodes is labeled an ECG. The former group, i.e., EGM, include intracardiac electrograms (IEGMs). In either instance, a cardiac electrogram typically exhibits certain standard features such as a P wave, an R wave, an S wave, a Q wave, a T wave, a QRS complex, etc. Where contraction of a chamber of the heart occurs responsive to delivery of an electrical stimulus, then the electrical waveform may be considered an evoked response (ER) and labeled an A wave, a V wave, etc., depending on the chamber, or chambers, stimulated. Also, an IEGM can include information to determine a paced propagation delay, generally defined as the difference between the delivery time of an electrical stimulus and a feature of an ER caused by the electrical stimulus. In some instances, a paced propagation delay may be defined on another basis, for example, based on a minimum in amplitude for an ER, maximum slope of an ER, etc., as used by an ER detection algorithm.

Various studies have related cardiac electrograms to damage. For example, subendocardial ischemia can prolong local recovery time. Since repolarization normally proceeds in an epicardial-to-endocardial direction, delayed recovery in the subendocardial region due to ischemia does not reverse the direction of repolarization but merely lengthens it. This generally results in a prolonged QT interval or increased amplitude of the T wave or both as recorded by the electrodes overlying, or otherwise sensing activity at, the subendocardial ischemic region.

Subepicardial or transmural ischemia is typically said to exist when ischemia extends subepicardially. This type of damage has a more visible effect on recovery of subepicardial cells compared with subendocardial cells. Recovery is more delayed in the subepicardial layers, and the subendocardial muscle fibers often seem to recover first. Repolarization is endocardial-to-epicardial, resulting in inversion of the T waves in leads overlying, or otherwise sensing activity at, the ischemic regions.

Injury to myocardial cells results when an ischemic process is more severe. Subendocardial injury on a surface ECG (i.e., an ECG) is typically manifested by ST segment depression while, in contrast, subepicardial or transmural injury is manifested as ST segment elevation. In patients with coronary artery disease, ischemia, injury and myocardial infarction of different areas can coexist and produce mixed and complex ECG patterns.

The term infarction describes necrosis or death of myocardial cells. Atherosclerotic heart disease is the most common underlying cause of myocardial infarction. The left ventricle is the predominant site for infarction; however, right ventricular infarction occasionally coexists with infarction of the inferior wall of the left ventricle. The appearance of pathological Q waves is the most characteristic ECG finding of transmural myocardial infarction of the left ventricle. A pathological Q wave is defined as an initial downward deflection of a duration of about 40 ms or more in any lead of a multi-lead surface ECG unit (except lead III and lead aVR). The Q wave appears when the infracted muscle is electrically inert and the loss of forces normally generated by the infarcted area leaves unbalanced forces of variable magnitude in the opposite direction from a remote region or zone (e.g., an opposite wall). These forces can be represented by a vector directed away from the site of infarction and seen as a negative wave (Q wave) by electrodes overlying, or otherwise sensing activity at, the infarcted region.

During acute myocardial infarction, the central area of necrosis is generally surrounded by an area of injury, which in turn is surrounded by an area of ischemia. Thus, various stages of myocardial damage can coexist. One commonly used distinction between ischemia and necrosis is whether the phenomenon is reversible. Transient myocardial ischemia that produces T wave, and sometimes ST segment abnormalities, can be reversible without producing permanent damage and is not accompanied by serum enzyme elevation.

Two types of myocardial infarction can be typically observed electrocardiographically: Q wave infarction and Non-Q wave infarction. Q wave infarction, which is diagnosed by the presence of pathological Q waves and is also called transmural infarction. However, transmural infarction is not always present, hence, the term Q-wave infarction may be preferable for ECG description. Non-Q wave infarction is typically diagnosed based on the presence of ST depression and T wave abnormalities. Elevation of serum enzymes is expected in both types of infarction. In the absence of enzyme elevation, ST and T wave abnormalities are interpreted usually as due to injury or ischemia rather than infarction.

As already mentioned, a damage site (e.g., ischemia, injury, infarction) can be localized to some extent using cardiac electrograms, for example, the general location of an infarct can be detected by an analysis of a 12-lead ECG. Leads that best detect changes in commonly described locations are classified as follows: Inferior (or diaphragmatic) wall—II, II and aVF; Septal—V1 and V2; Anteroseptal—V1, V2, Vf3 and sometimes V4; Anterior—V3, V4 and sometimes V2; Apical—V3, V4 or both; Lateral—I, aVL, V5 and V6; and Extensive anterior—I, aVL and V1 through V6.

Posterior wall infarction does not typically produce Q wave abnormalities in conventional leads and is generally diagnosed in the presence of tall R waves in V1 and V2. The classic changes of necrosis (Q waves), injury (ST elevation), and ischemia (T wave inversion) may all be seen during acute infarction. In recovery, the ST segment is the earliest change that normalizes, then the T wave; the Q wave usually persists. Therefore, the age of the infarction can be roughly estimated from the appearance of the ST segment and T wave. The presence of the Q wave in the absence of ST and T wave abnormality generally indicates prior or healed infarction. Although the presence of a Q wave with a 40 ms duration is usually sufficient for diagnosis, criteria defining the abnormal depth of Q waves in various leads have been established. For example, in lead I, the abnormal Q wave must be more than 10 percent of QRS amplitude; in leads II and aVF, it should exceed 25 percent; and in aVL it should equal 50 percent of R wave amplitude. Q waves in V2 through V6 are typically considered abnormal if greater than 25 percent of R wave amplitude.

A deep Q wave generally indicates myocardial necrosis, although similar patterns may be produced by other conditions, such as WPW syndrome, connected transportation of the great vessels, etc. ST-segment elevation can be observed in conditions other than acute myocardial infarction.

With respect to ST segment elevation, other causes of ST segment elevation include the following: acute pericarditis (ST elevation in acute pericarditis is generally diffuse and does not follow the pattern of blood supply. As a rule these changes are not accompanied by reciprocal depression of the ST segment in other leads); early repolarization (In some patients without known heart disease, particularly young patients, early takeoff of the ST segment may be seen); ventricular aneurysm (after acute myocardial infarction, the ST segment usually normalizes. However, in the presence of a persistent aneurysm in the region of infarction, ST segment elevation may persist indefinitely).

Abnormal T waves can be seen in a variety of conditions other than myocardial ischemia, including: hyperventilation, cerebrovascular disease, mitral valve prolapse, right or left ventricular hypertrophy, conduction abnormalities (right or left bundle branch block), ventricular preexcitation, myocarditis, electrolyte imbalance, cardioactive drugs such as digitalis and antiarrhythmic agents, or for no obvious cause (particularly in women).

Figure 6:
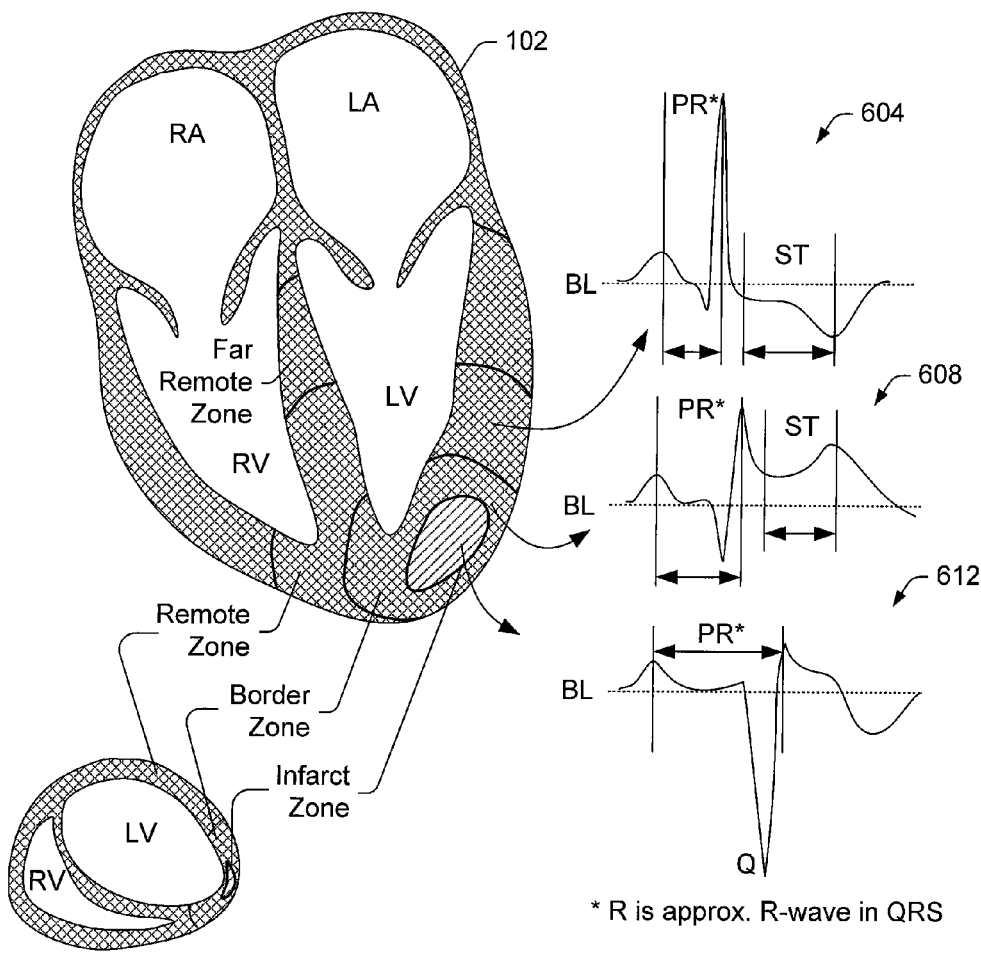
FIG. 6 is diagram of a heart and cardiac electrograms along with exemplary criteria for assessing cardiac condition.

Thus, cardiac electrograms may provide insight into location, severity, age, repair, etc., of myocardial tissue damage (e.g., ischemia, injury and/or infarct). FIG. 6 shows cardiac infarct and electrical information 600 in the form of two cross-sectional views of the heart 102 along with a series of cardiac electrograms 604, 608, 612 and exemplary criteria 640 for use analyzing one or more cardiac electrograms. In the block 640, the term "J point" refers to the point at which the QRS complex meets the ST wave. Also, for FIG. 6, the R* refers specifically to the R-wave of a QRS complex. In other instances, R refers generally to an intrinsic ventricular event (e.g., ventricular contraction due to AV nodal conduction whether originating from intrinsic or electrically stimulated atrial activity).

The remote zone cardiac electrogram 604 exhibits a depressed ST segment and may represent an ischemic or injured region. The border zone cardiac electrogram 608 exhibits an elevated ST segment and a prolonged PR segment and may represent subepicardial or transmural injury. The infarct zone cardiac electrogram 612 exhibits a deep Q wave, which generally indicates myocardial necrosis, i.e., infarct.

Electrical information may be acquired from patient populations (e.g., prior infarct, heart failure, normal, young, old, etc.) and used for purposes of analyzing electrical information for a particular patient. For example, electrical information for healthy patients may be used to establish one or more standard segments (e.g., standard time for ST segment, standard amplitude for ST, Q, PR, etc.). One or more of such standards may then be used to assess cardiac condition of a particular patient. In a specific example, PR and ST interval times are acquired for a patient and compared to standard PR and ST interval times. The comparison may be a ratio based comparison (e.g., PR/ST, ST/PR, etc.), a percentage based comparison, etc., where the comparison can help assess a region of the patient's heart with respect to an infarct (e.g., distance of region from an infarct zone, damage level, etc.).

Various exemplary methods include acquiring one or more cardiac electrograms and analyzing the one or more cardiac electrograms to determine health of a myocardial region. For example, the modules 430 of FIG. 4 may program the implantable device 100 of FIGS. 1 and 2 to perform such a method and to allow for selection of an anti-arrhythmia therapy based in part on health of a myocardial region.

Figure 7:
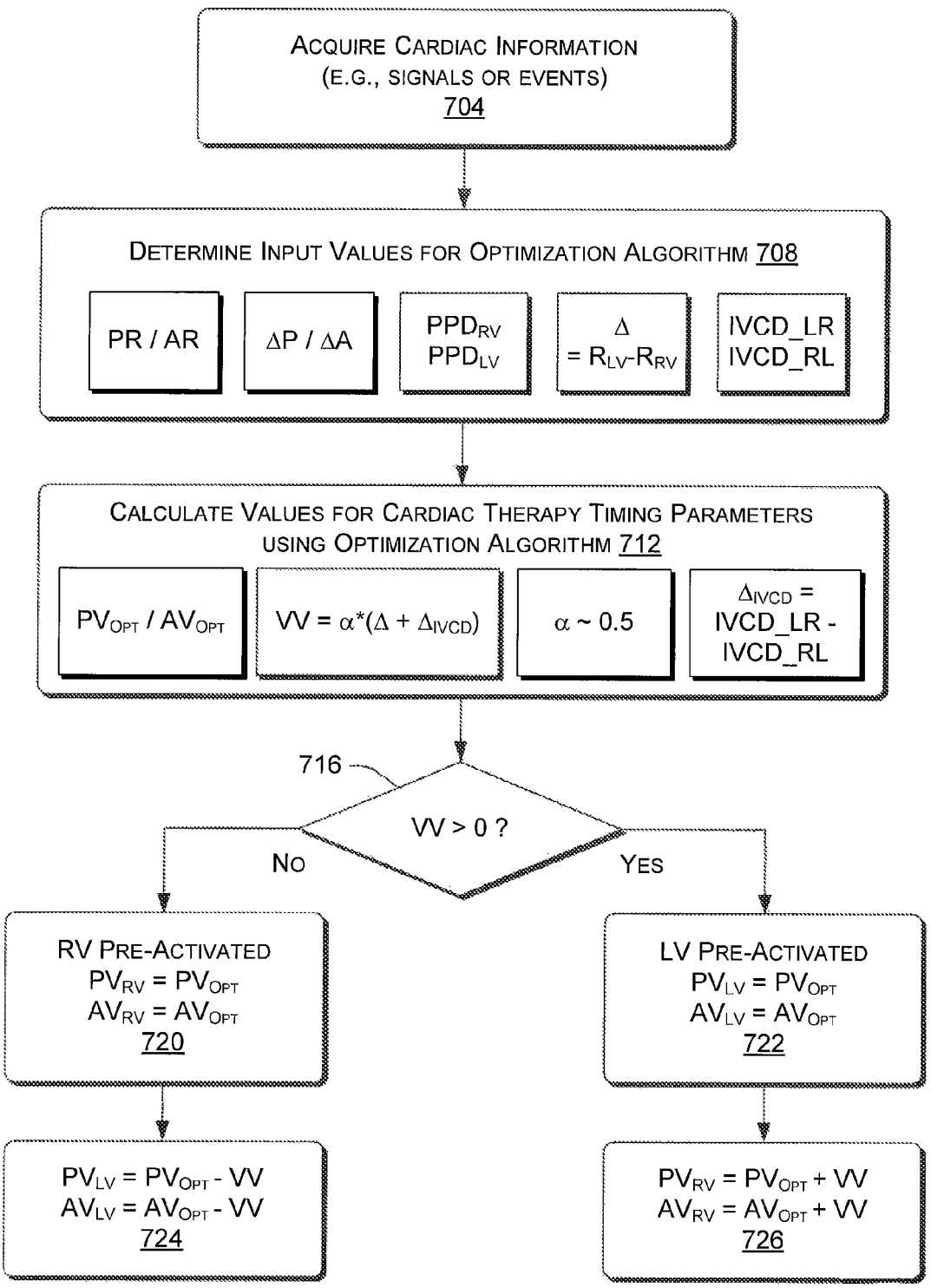
FIG. 7 is a block diagram of an exemplary method for optimizing one or more cardiac pacing parameters.

With respect to the multi-site pacing module 414 of FIG. 4, such a module may rely on the method 700 of FIG. 7 to determine one or more pacing parameters. Specifically, the method 700 pertains to parameter optimization (e.g., for CRT and/or bi-ventricular pacing or, more generally, pacing that may use more than one stimulation site).

As described herein, an anti-arrhythmia therapy can halt or alter a particular pacing therapy. For example, if a patient is subject to biventricular pacing using a VV delay specified by the method 700 of FIG. 7 and an arrhythmia is detected then control logic may halt or alter delivery of the pacing therapy for purposes of delivering an anti-arrhythmia therapy. Such an anti-arrhythmia therapy may rely on a VV delay parameter (e.g., $VV_{ATP}$) that differs from the VV delay parameter of the method 700 of FIG. 7. After delivery of a selected anti-arrhythmia therapy or therapies (e.g., tiered therapy), pacing may resume according to one or more parameters determined using the method 700 of FIG. 7.

Various delays or parameters discussed herein include:

| | |
|---|---|
| PP, AA | Interval between successive atrial events |
| PV | Delay between an atrial event and a paced ventricular event |
| $PV_{optimal}$ | Optimal PV delay |
| $PV_{RV}$ | PV delay for right ventricle |
| $PV_{LV}$ | PV delay for left ventricle |
| AV | Delay for a paced atrial event and a paced ventricular event |
| $AV_{optimal}$ | Optimal AV delay |
| $AV_{RV}$ | AV delay for right ventricle |
| $AV_{LV}$ | AV delay for left ventricle |
| Δ | Estimated interventricular delay, e.g., via IEGM, etc. |
| $\Delta_{programmed}$ | Programmed interventricular delay (e.g., a programmed VV delay) |
| $\Delta_{optimal}$ | Optimal interventricular delay, e.g., via hemodynamic sensing/sensor or other cardiac sensing |
| IVCD_RL | Delay between an RV event and a consequent sensed LV event |
| IVCD_LR | Delay between an LV event and a consequent sensed RV event |
| $\Delta_{IVCD}$ | Interventricular conduction delay |
| ΔP, ΔA | Width of an atrial event |
| DD, AD | Interval between end of an atrial wave (e.g., P or A wave) and beginning of a R or QRS complex or other appropriate point |
| ΔDD, ΔAD | $DD_{LV} - DD_{RV}$ or $AD_{LV} - AD_{RV}$ |
| PPD | Paced propagation delay (e.g., time from delivery of |

-continued stimulation to an evoked response or feature of an evoked response)

In FIG. 7, the method 700 commences in an acquisition block 704 that acquires cardiac information. Cardiac information may be in the form of signals, events or a combination of signals and events. For example, a detection algorithm may detect an atrial event and a ventricular event and note a time for each of these events. With respect to signals, the acquisition block 704 may acquire electrograms that can be analyzed after their acquisition for any of a variety of features (e.g., a maximum slope as indicative of an evoked response, etc.).

In the example of FIG. 7, the method 700 includes a determination block 708 that determines input values for an optimization algorithm that can optimize timing parameters for delivery of cardiac therapy such as CRT. The input values shown in FIG. 7 include PR/AR, $\Delta P/\Delta A$, $PPD_{RV}/PPD_{LV}$, $\Delta$, IVCD_LR and IVCD_RL.

According to the method 700, a calculation block 712 calculates values for cardiac therapy timing parameters using the optimization algorithm. While the example of FIG. 7 refers to an optimization algorithm, programmer or device based software, or a look-up table may be used to determine the values of block 712. As indicated, the calculation block 712 calculates an optimum value for the parameter PV or AV (e.g., $PV_{Opt}$ or $AV_{Opt}$) and, for bi-ventricular pacing, it calculates an optimum value for VV. For example, VV may be calculated using the following equation: $VV=\alpha^*(\Delta+\Delta_{IVCD})$ where $\alpha$ is a parameter assigned a value based on experience, patient performance data, etc. In practice, a value for $\alpha$ of about 0.5 has been used with good results.

Upon calculation of a value for the parameter VV, the method 700 enters a decision block 716 that decides if VV exceeds zero. The decision made by the decision block 716 dictates whether ventricular pacing should occur in first in the right ventricle or first in the left ventricle. In FIG. 7, if VV does not exceed zero then the right ventricle is paced first, as indicated in a block 720 "RV Pre-Activated" or "RV Master and LV Slave". However, if VV does exceed zero then the left ventricle is paced first, as indicated in a block 722 "LV Pre-Activated" or "LV Master and RV Slave". In either instance, a block follows 724 or 726, respectively, that calculates the PV or AV timing of the other ventricle based on VV. The various signs used in the method 700 rely on convention and may differ where the equations for $\Delta$ and $\Delta_{IVCD}$ differ.

Referring again to the parameter $\alpha$, a comparison between $\Delta$ and $\Delta_{programmed}$ or $\Delta_{optimal}$ can indicate a difference between a current cardiac therapy or state and a potentially better cardiac therapy or state. For example, consider the following equation:

$$\alpha=\Delta_{optimal}/\Delta$$

where $\alpha$ is an optimization parameter. Various echocardiogram and tissue Doppler image technique can be used to determine patient specific $\alpha$. However echocardiographic studies indicate that the parameter $\alpha$ is typically about 0.5. The use of such an optimization parameter is optional. The parameter $\alpha$ may be used as follows:

$$VV=\alpha^*(\Delta+\Delta_{IVCD})$$

If a parameter such as the aforementioned a parameter is available, then such a parameter is optionally used to further adjust and/or set one or more delays, as appropriate.

In many instances, heart condition will affect $AR_{RV}$ and $AR_{LV}$ (or $PR_{RV}$ and $PR_{LV}$) and IVCD (e.g., IVCD-RL and/or IVCD-LR), which, in turn, may affect an existing optimal VV delay setting. Various exemplary methods, devices, systems, etc., include triggering of an algorithm to update an existing optimal VV delay according to a predetermined time or event period or activity sensors for exercise, resting, etc. An exemplary device may include a learning method that learns based on differences in conduction times (e.g., $AR_{RV}$ and $AR_{LV}$, IVCD, etc.) such that parameters associated with different heart demands can be stored. The exemplary learning method may then extract such learned or other parameters to set an optimal VV delay.

In the aforementioned learning example, if the device learns on the basis of different cardiac demands, the device may adjust AV delay and/or VV delay and/or learn a new AV delay and/or VV delay upon a change in cardiac demand. According to this example, use of external measurement or sensing equipment (e.g., echocardiogram, etc.) is optional. Further, use of internal measurement or sensing equipment for sensing pressure or other indicators of hemodynamic performance is optional. Again, adjustment and learning may rely on IEGM information and/or cardiac other rhythm information.

An exemplary method relies on an atrial to right ventricular conduction time, an atrial to left ventricular conduction time and a $\alpha$ parameter, for example, as described above, to determine an optimal AV delay and/or VV delay. Another exemplary method relies on an atrial to right ventricular conduction time, an atrial to left ventricular conduction time and a limit that may be used to decide whether one or more of the conduction times are acceptable. In these examples, an interventricular conduction time may be used in lieu of an atrial to ventricular conduction time, for example, where ventricular activity originates with a common atrial event.

According to various exemplary methods, devices, systems, etc., information acquired (e.g., sensed, detected and/or determined) may be used to diagnose cardiac condition. For example, an exemplary method may track AV delays and/or VV delays over time. Such information may then be used to determine subsequent therapy.

Various exemplary methods, devices, systems, etc., include determining an optimal interventricular delay (e.g., $\Delta_{optimal}$) using a modality such as an echocardiogram. While an internal echocardiogram or implantable hemodynamic sensors may be available or become available and be able to measure such optimal delays for a variety of patient circumstances (e.g., sleep, exercise, etc.), an exemplary method, device, system, etc., includes use of one or more internal sensors to measure and/or update such an optimal delay and/or to determine values for one or more parameters related to an optimal delay. For example, a blood pressure sensor (e.g., aortic arch, left atrium, etc.) may be used to determine or to update an optimal delay. Further, information may be collected over a period of time to determine heart condition (e.g., deterioration, improvement, etc.).

In general, an optimal interventricular delay will change as demand and/or heart conditions change. Thus, an exemplary method may determine an optimal interventricular delay during sleep on a nightly, a weekly or some other basis. Such an exemplary method may determine an optimal interventricular delay within a matter of minutes (e.g., approximately 5 heart beats). Such an exemplary method may be triggered according to a change in heart rate or some other parameter related to heart condition. Over time or at time of programming, an exemplary device may store one or more optimal interventricular delays as a function of heart rate, heart condition, etc., and then implement a selected delay from the stored delays upon occurrence of a rate, condition, etc., or a change in rate, condition, etc. Such dynamic control of interventricular delay can improve cardiac performance and potentially allow for an improvement in patient quality of life (e.g., allow for a broader range of patient activity). If after some predetermined period of time or upon occurrence of a particular condition, an exemplary device may indicate a need for a more rigorous determination, for example, via an echocardiogram.

Figure 8:
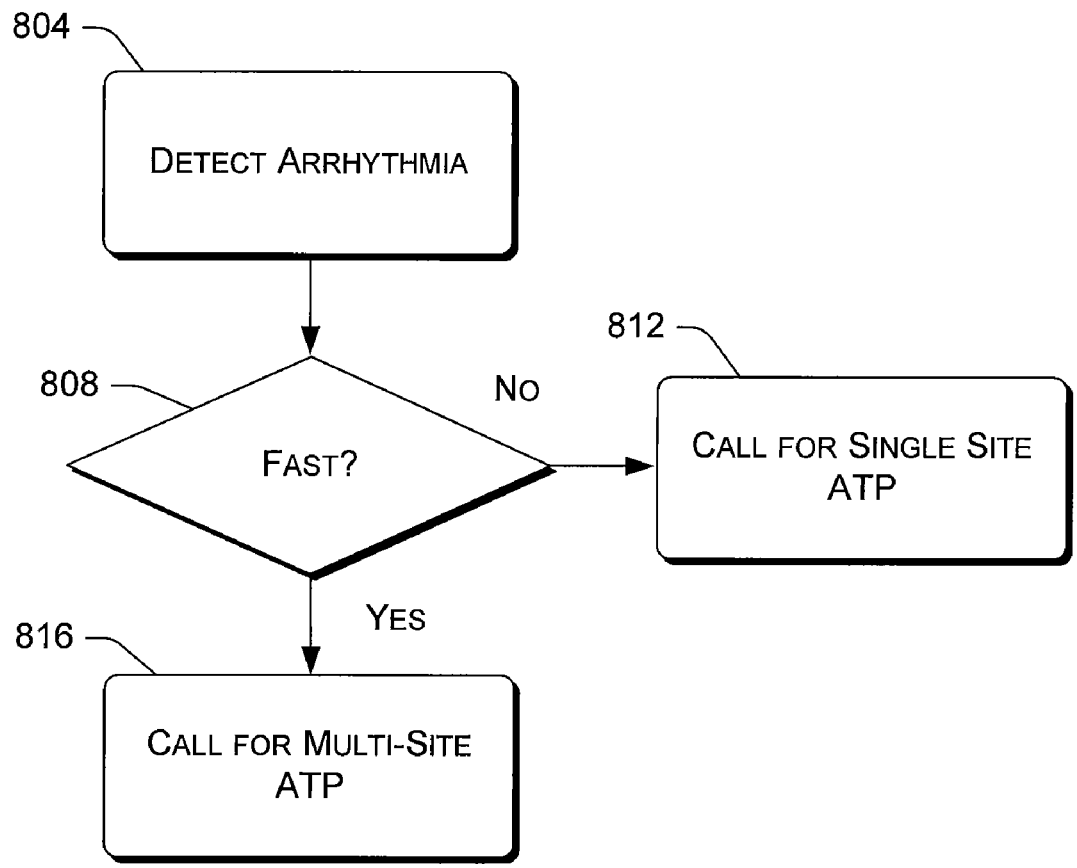
FIG. 8 is a block diagram of an exemplary method for deciding whether to call for single site anti-tachycardia pacing or multi-site anti-tachycardia pacing.

FIG. 8 shows an exemplary method 800 for deciding whether to deliver single site anti-tachycardia pacing therapy or multi-site anti-tachycardia pacing therapy in response to detection of an arrhythmia. The method 800 commences in a detection block 804 and then enters a decision block 808. The decision block 808 decides whether the detected arrhythmia is a fast arrhythmia. For example, the criteria explained above with respect to the study of Gasparini may be used to decide what is "fast" (see, e.g., tables 510, 520 of FIG. 5). Alternatively, information specific to a patient or a group of patients may determine what is fast, especially where the information allows for an increased success of termination of arrhythmias. In other words, such information may allow for determination of a threshold rate where a heart rate above the threshold rate is considered "fast".

According to the method 800, if the detected arrhythmia is not "fast" then a block 812 calls for single site ATP. For example, where a patient has an implantable device with multiple leads, the block 812 calls for delivery of ATP using a single one of the leads and, more particularly, a single site (e.g., a closely spaced pair or set of electrodes) where the determination as to the lead, the site, etc., may be made by the implantable device. Alternatively, if the detected arrhythmia is "fast" then a block 816 calls for delivery of multi-site ATP where the determination as to multiple delivery sites may be made by the implantable device. For example, where a patient has an implantable device with multiple leads, the block 816 can call for delivery of ATP using two of the leads. In this example, the block 816 may call for use of a single site (e.g., a closely spaced pair or set of electrodes) on one of the leads and a single site (e.g., a closely spaced pair or set of electrodes) on another of the leads. In another example, the block 816 may call for delivery of ATP using two sites of a single lead (e.g., consider the lead 106, which includes various spaced electrodes that may define multiple sites).

In a particular example, an implantable device may be configured with respect to multiple zones and a rate determination applied in relationship to a zone or zones. Such a device may be programmed with information to define zones or may execute an algorithm that acquires information and then defines one or more zones based at least in part on the acquired information. If a patient undergoes clinical testing that may shed light on existence of zones or changes in zones (e.g., zone boundaries), such information may be used to update an implantable device. In various examples, an implantable device may account for information indicative of ischemic or non-ischemic disease etiology and information and be utilized to determine whether RV only (e.g., for non-ischemic) or Bi-V (e.g., for ischemic) therapies are suitable.

In the multi-site scenarios, various modules of FIG. 4 may determine an $SS_{ATP}$ delay that dictates a time delay between a delivery time for anti-arrhythmia energy at one of the sites with respect to a delivery time for anti-arrhythmia energy at another one of the sites. Where one site is a right ventricular site and another site is a left ventricular site then the delay may be referred to as a $VV_{ATP}$ delay (e.g., for anti-tachycardia pacing).

Figure 9:
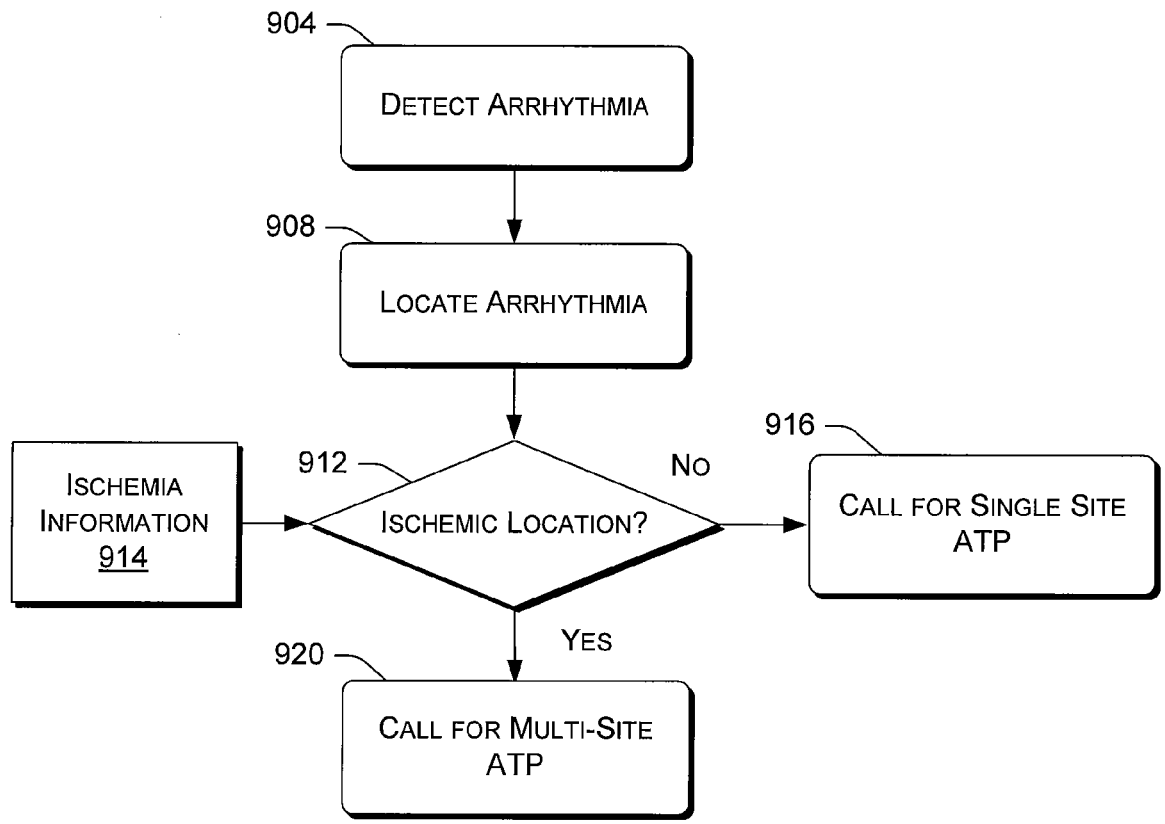
FIG. 9 is a block diagram of an exemplary method for deciding whether to call for single site anti-tachycardia pacing or multi-site anti-tachycardia pacing based in part on ischemia.

FIG. 9 shows an exemplary method 900 for deciding whether to deliver single site anti-tachycardia pacing therapy or multi-site anti-tachycardia pacing therapy in response to detection of an arrhythmia. The method 900 commences in a detection block 904 and then enters a location block 908 that aims to locate the arrhythmia. A decision block 912 follows that relies on ischemia information 914 (see, e.g., the information 600 of FIG. 6). If the decision block 912 decides that the detected arrhythmia is not located at or proximate to an ischemic location then a call block 916 calls for single site ATP. However, if the decision block 912 decides that the detected arrhythmia is located at or proximate to an ischemic location then a call block 920 calls for multi-site ATP. For example, where a patient has an implantable device with multiple leads, the block 920 calls for delivery of ATP using two of the leads. In this example, the block 920 may call for use of a single site (e.g., a closely spaced pair or set of electrodes) on one of the leads and a single site (e.g., a closely spaced pair or set of electrodes) on another of the leads. In another example, the block 920 may call for delivery of ATP using two sites of a single lead (e.g., consider the lead 106, which includes various spaced electrodes that may define multiple sites).

In the multi-site scenarios, various modules of FIG. 4 may determine an $SS_{ATP}$ delay that dictates a time delay between a delivery time for anti-arrhythmia energy at one of the sites with respect to a delivery time for anti-arrhythmia energy at another one of the sites. Where one site is a right ventricular site and another site is a left ventricular site then the delay may be referred to as a $VV_{ATP}$ delay (e.g., for anti-tachycardia pacing).

Figure 10:
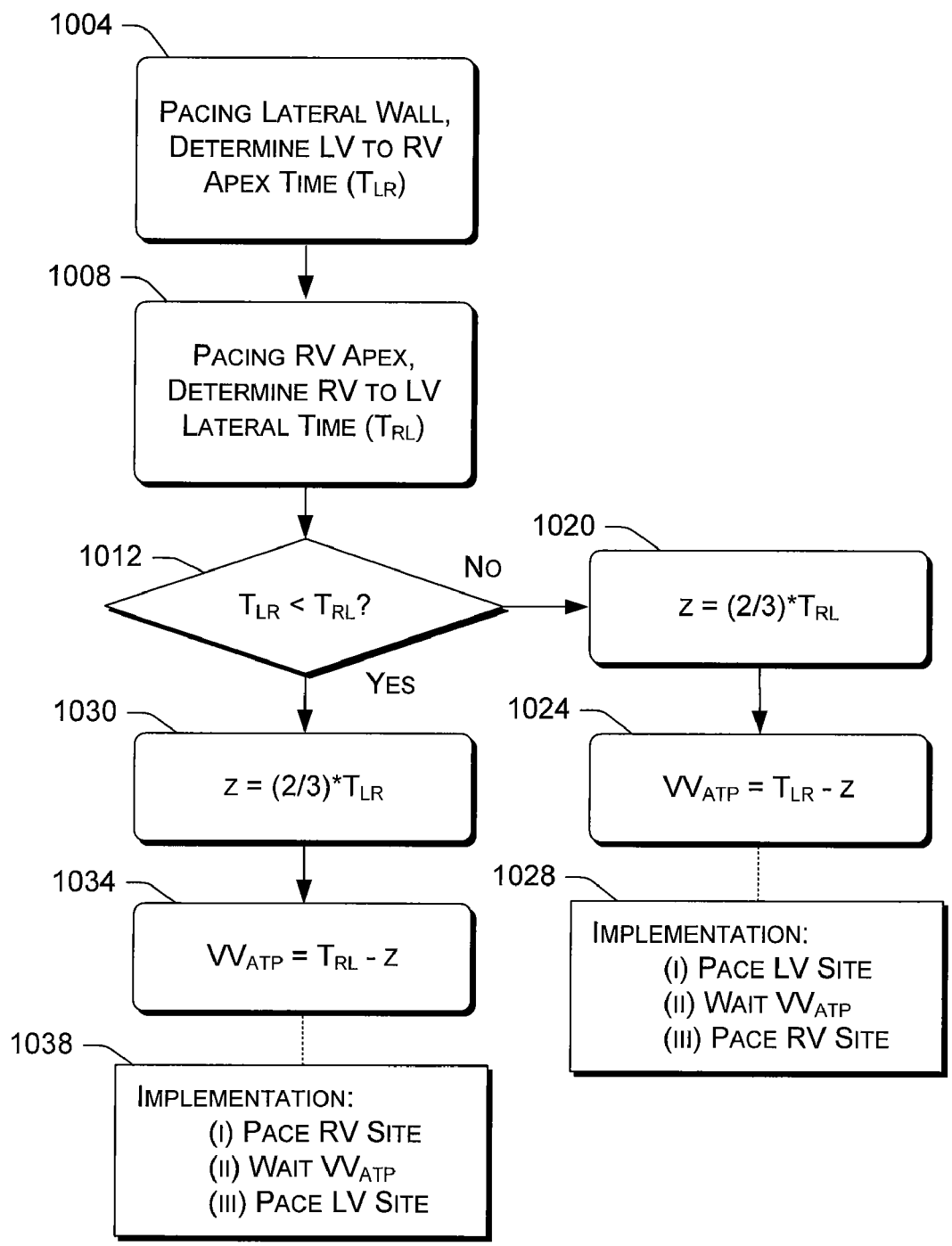
FIG. 10 is a block diagram of an exemplary method for calculating a site-to-site delay for anti-tachycardia pacing based on directional conduction times.

FIG. 10 shows an exemplary method 1000 that refers to particular pacing sites. The method 1000 includes a determination block 1004 that determines an LV lateral wall to RV apex time ($T_{LR}$) by delivering energy to a LV lateral wall site and by sensing the delivered energy at a RV apex site. For example, in FIG. 3 the LV lateral wall site may be determined by the electrode pair 122, 123(i) of the left ventricular lead 106 and the RV apex site may be determined by the electrode pair 128, 130 of the right ventricular lead 108. The method 1000 also includes a determination block 1008 that determines an RV apex to LV lateral wall time ($T_{RL}$) by delivering energy to a RV apex site and by sensing the delivered energy at a LV lateral wall site. For example, in FIG. 3 the LV lateral wall site may be determined by the electrode pair 122, 123(i) of the left ventricular lead 106 and the RV apex site may be determined by the electrode pair 128, 130 of the right ventricular lead 108. In general, the sites used in the blocks 1004, 1008 are the same (reciprocal), however, depending on device configuration, sensing may be achieved via unipolar arrangements (e.g., using a can electrode) where only a single lead-based electrode is used. Other variations are possible as well.

After determining the times $T_{LR}$ and $T_{RL}$, the method 1000 continues at a decision block 1012 that decides which conduction time is the lesser of the two. For example, in the example of FIG. 10, the decision block 1012 decides if $T_{LR}$ is less than $T_{RL}$. If $T_{LR}$ is not less than $T_{RL}$ then the method 1000 enters a calculation block 1020 that calculates a parameter z as $(2/3)*T_{RL}$. To the contrary, if $T_{LR}$ is less than $T_{RL}$ then the method 1000 enters a calculation block 1030 that calculates a parameter z as $(2/3)*T_{LR}$. The two branches of the decision block 1012 ultimately calculate a $VV_{ATP}$ delay. In a calculation block 1024, the $VV_{ATP}$ delay is calculated as $T_{LR}-z$; whereas in a calculation block 1034, the $VV_{ATP}$ delay is calculated as $T_{RL}-z$.

Given the calculated $VV_{ATP}$ delay, an anti-arrhythmia therapy (e.g., anti-tachycardia pacing therapy) can deliver anti-arrhythmia pacing to via the RV site and via the LV site using the $VV_{ATP}$ delay in an effort to optimize delivery of the associated waveforms to the arrhythmic site or region. For example, an implementation block 1028 describes implementation of the $VV_{ATP}$ of the block 1024 as pacing the LV site, waiting $VV_{ATP}$ and then pacing the RV site, where the pacing aims to terminate a detected arrhythmia. Similarly, an implementation block 1038 describes implementation of the $VV_{ATP}$ of the block 1034 as pacing the RV site, waiting $VV_{ATP}$ and then pacing the LV site, where the pacing aims to terminate a detected arrhythmia. In both instances, the site associated with the longer conduction time is paced first (for branch 1020, $T_{LR}$ is longer and for branch 1030, $T_{RL}$ is longer).

In the method 1000, the factor (⅔) arises from a three zone model as shown in FIG. 3 (e.g., a conduction time can be divided by three to provide an average per zone conduction time). While the example of FIG. 10 uses the factor (⅔), other factors or equations may be used where information exists as to the location of an arrhythmic focus or zone. In general, the approach of the method 1000 aims to account for directional conduction characteristics in an effort to increase the amount of tissue depolarized at a given point in time. The method 1000 of FIG. 10, or variation thereof (e.g., for different sites), may be included in the methods 800 and 900 where they call for multi-site anti-arrhythmia therapy.

Figure 11:
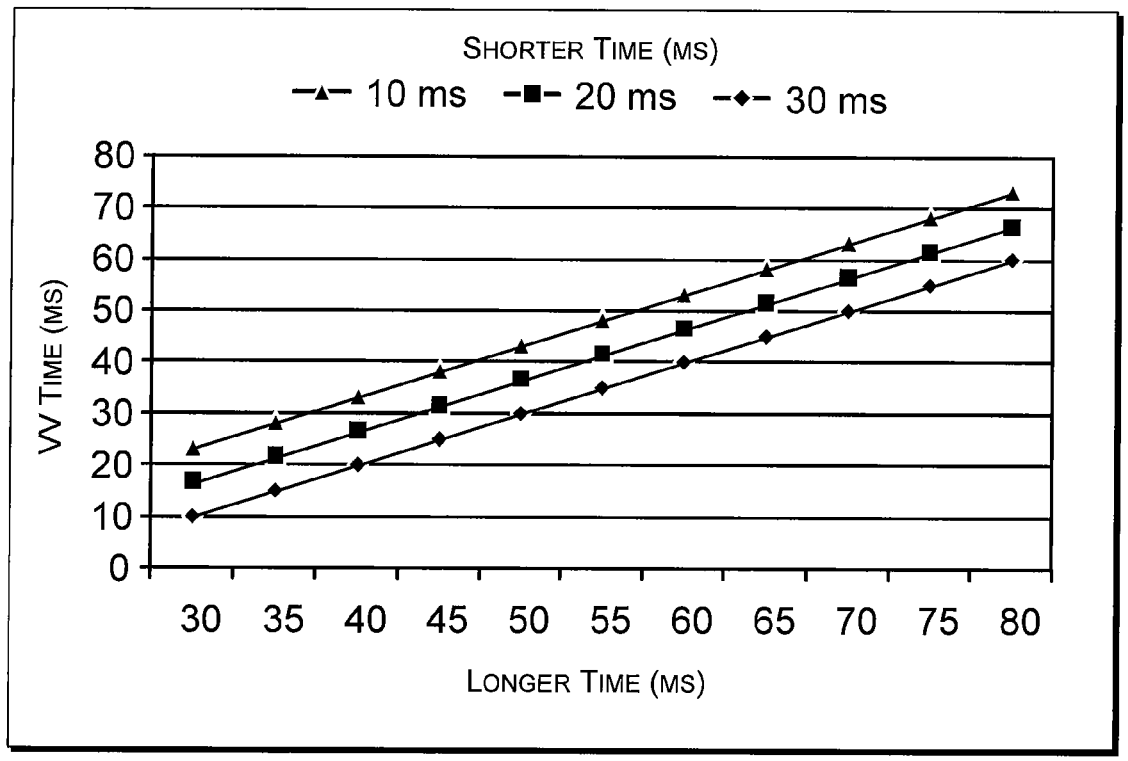
FIG. 11 is a plot of site-to-site delays versus a directional conduction time for various constant directional conduction time values.

FIG. 11 shows a plot 1100 of VV time versus "longer" conduction time, according to the calculations of the method 1000 of FIG. 10. The lines in the plot 1100 correspond to constant "shorter" times of 10 ms, 20 ms and 30 ms. Such information may be optionally programmed in memory of an implantable device to avoid one or more calculations. Such a plot may be modified due to patient particularities, for example, success and/or failure of an anti-arrhythmia therapy.

In the method 1000 and the plot 1100, if the $T_{RL}$ and $T_{LR}$ are both about 10 ms, the offset would be 3.33 ms, with both about 12 ms the offset would be 4 ms, etc. and one would be greater than the other. However, where $T_{RL}$ and $T_{LR}$ are less than about 10 ms then the offset may be set to approximately 0 ms (or other minimum value as dependent on hardware and/or software characteristics of an implantable device). The method 1000 may rely on a threshold value or values for a "long" conduction time and a "short" conduction time. For example, if the conductions are not both greater than 10 ms then the offset ($VV_{ATP}$) is set to 0 ms.

Various exemplary methods described herein aim to improve efficacy in terminating sustained monomorphic VT compared to traditional right ventricular anti-tachycardia pacing ($RV_{ATP}$) in patients undergoing VT ablation. An exemplary method acquires information for a group of such patients where efficacy of ATP therapy (e.g., RV burst 90%/10 pulses) is compared to an algorithm that utilizes a biventricular ATP scheme with a $VV_{ATP}$ delay or offset (e.g., according to the method 1000 of FIG. 10). Such information can be analyzed to determine when fewer pulses are required.

An exemplary method may optionally initiate VT and then apply an anti-arrhythmia therapy to terminate the initiated VT. Upon induction, a tachycardia cycle length and successful termination with right ventricular burst pacing can be assessed utilizing a burst sequence of approximately 10 paces at 90% of the VT cycle length. An ablation catheter (e.g., as a surrogate for chronically implanted left ventricular lead) may be placed on the lateral wall of the left ventricle. Given such an arrangement, conduction time $T_{RL}$, $T_{LR}$ can be measured and used to determine the $VV_{ATP}$ offset. After an initial determination, a subsequently induced VT can be followed with an ATP pacing algorithm using the determined $VV_{ATP}$, for example, with 3 stimuli, then 4 stimuli, then 5 stimuli in succession. Results can be compared to the results of RV burst pace sequences to compare rates of successful termination of the tachycardia.

Upon performance of such a regimen in a single patient or a group of patients, an implantable device may be suitably configured and programmed to delivery ATP responsive to arrhythmias. For example, such a device may be programmed to perform various exemplary methods presented herein.

Figure 12:
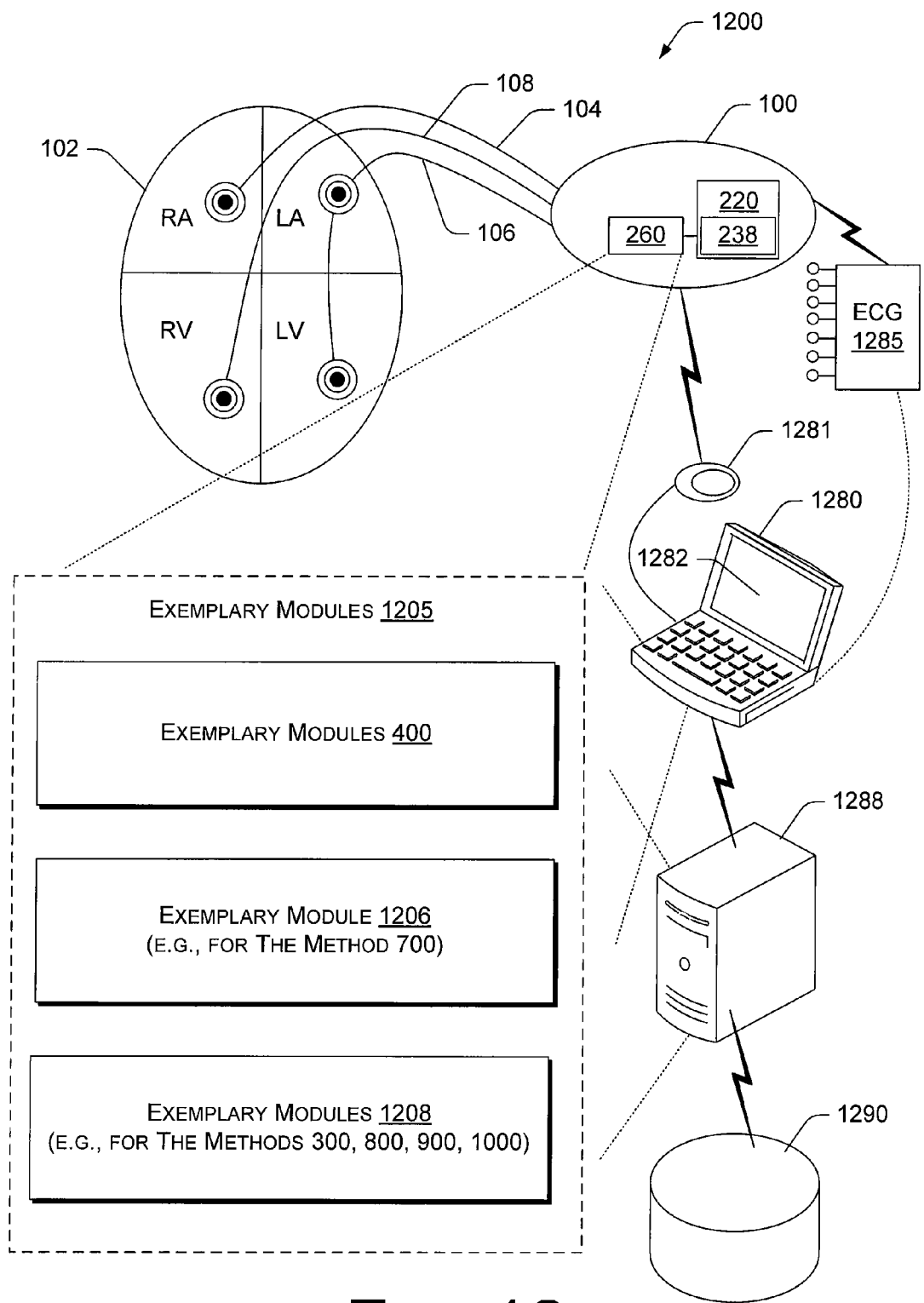
FIG. 12 is a diagram of an exemplary system capable of implementing various methods.

FIG. 12 shows an exemplary system 1200 that includes the exemplary implantable device 100 of FIGS. 1 and 2, with processor 220 including one or more modules 1205, for example, that may be loaded via memory 260. A series of leads 104, 106 and 108 provide for delivery of stimulation energy and/or sensing of cardiac activity, etc., associated with the heart 102. Stylized bullets indicate approximate positions or functionality associated with each of the leads 104, 106 and 108. Other arrangements are possible as well as use of other types of sensors, electrodes, etc.

Memory 260 is shown as optionally including one or more of the modules 1205. The modules 1205 pertain to specific methods and/or algorithmic options for CRT and are described further below. In some circumstances, part of a method may be performed using a device other than the implantable device 100. For example, for acquisition of ECG information, an ECG unit 1285 may be used, which optionally communicates with the device 100 or one or more other devices (e.g., the device 1280, 1288, etc.).

The system 1200 may include other modules not shown in FIG. 12 for purposes such as programming the implantable device 100, performing measurements, determinations or calculations, displaying information, etc. For example, a module may cause a programmer device 1280 to display control graphics on a display 1282 whereby a clinician can actuate instructions via an associated displayed graphic to cause the implantable device 100 to measure directional conduction times (e.g., $T_{RL}$, $T_{LR}$), to communicate values to the device 1280 and to display the values on the display 1282 of the device 1280. Such an arrangement can allow a clinician to set an offset for delivery of multi-site anti-arrhythmia therapy (e.g., multi-site ATP).

In the example of FIG. 12, the system 1200 includes the device programmer 1280 having a wand unit 1281 for communicating with the implantable device 100. The programmer 1280 may further include communication circuitry for communication with another computing device 788, which may be a server. The computing device 1280 may be configured to access one or more data stores 1290, for example, such as a database of information germane to a patient, an implantable device, therapies, etc.

The programmer 1280 and/or the computing device 1288 may include modules that complement or interact with the modules 1205, noting that a particular implementation of a method may use more than one device.

The programmer 1280 optionally includes features of the commercially available 3510 programmer and/or the MERLIN™ programmer marketed by St. Jude Medical, Sylmar, Calif. The MERLIN™ programmer includes a processor, ECC (error-correction code) memory, a touch screen, an internal printer, I/O interfaces such as a USB that allows a device to connect to the internal printer and attachment of external peripherals such as flash drives, Ethernet, modem and WiFi network interfaces connected through a PCMCIA/CardBus interface, and interfaces to ECG and RF (radio frequency) telemetry equipment. The programmer 1280 includes the display 782 for displaying one or more graphical user interfaces (GUIs).

The wand unit 1281 optionally includes features of commercially available wands. As shown, the wand unit 1281 attaches to the programmer 1280, which enables clinicians to conduct implantation testing and performance threshold testing, as well as programming and interrogation of pacemakers, implantable cardioverter defibrillators (ICDs), emerging indications devices, etc.

During implant, a system such as a pacing system analyzer (PSA) may be used to acquire information, for example, via one or more leads. A commercially available device marketed as WANDA™ (St. Jude Medical, Sylmar, Calif.) may be used in conjunction with a programmer such as the MERLIN™ programmer or other computing device (e.g., a device that includes a processor to operate according to firmware, software, etc.). Various exemplary techniques described herein may be implemented during implantation and/or after implantation of a device for delivery of electrical stimulation (e.g., leads and/or pulse generator) and the types of equipment for acquiring and/or analyzing information may be selected accordingly. For example, during implantation, a catheter may be used to determine an optimal site for a lead or one or more electrodes. In this example, arrhythmias may be induced and terminated to determine an optimal offset for an anti-arrhythmia therapy (ATT) that relies on multiple-sites (e.g., multi-site ATP).

The wand unit 1281 and the programmer 1280 allow for display of atrial and ventricular electrograms simultaneously during a testing procedure. Relevant test measurements, along with customizable implant data, can be displayed, stored, and/or printed in a comprehensive summary report for the patient's medical records and physician review and/or for other purposes.

In the example of FIG. 12, the data store 1290 may include information such as measures, values, scores, etc. Such information may be used by a model, in making a comparison, in making a decision, in adjusting a therapy, etc. Such information may be updated periodically, for example, as the device 100 (or other device(s)) acquires new patient information. The system 1200 is an example as other equipment, instructions, etc., may be used or substituted for features shown in FIG. 12.

In the example of FIG. 12, the exemplary modules 400 are shown along with exemplary module 1206 (e.g., for the method 700) and exemplary modules 1208 (e.g., for the methods 300, 800, 900, 1000).

CONCLUSION

Although exemplary methods, devices, systems, etc., have been described in language specific to structural features and/or methodological acts, it is to be understood that the subject matter defined in the appended claims is not necessarily limited to the specific features or acts described. Rather, the specific features and acts are disclosed as exemplary forms of implementing the claimed methods, devices, systems, etc.

What is claimed is:

1. A method comprising:
    delivering a pace using an electrode positioned on the lateral wall of the left ventricle of a heart;
    sensing the pace using an electrode positioned in the right ventricle of the heart;
    determining a left to right directional conduction time ($T_{LR}$);
    delivering a pace using an electrode positioned in the right ventricle of the heart;
    sensing the pace using an electrode positioned on the lateral wall of the left ventricle of the heart;
    determining a right to left directional conduction time ($T_{RL}$);
    calculating a site-to-site offset ($VV_{ATP}$) for multi-site anti-tachycardia pacing based on the left to right directional conduction time and the right to left directional conduction time; and
    instructing an implantable device to deliver multi-site anti-tachycardia pacing using the site-to-site offset ($VV_{ATP}$).

2. The method of claim 1 wherein the implantable device delivers the multi-site anti-tachycardia pacing using the site-to-site offset in response to detecting an arrhythmia.

3. The method of claim 2 wherein the arrhythmia comprises a ventricular tachycardia.

4. The method of claim 2 wherein the arrhythmia exceeds a predetermined rate threshold and thereby comprises a fast arrhythmia.

5. The method of claim 1 wherein the implantable device performs the delivering and the sensing.

6. The method of claim 5 wherein the implantable device performs the determining and the calculating.

7. The method of claim 1 wherein the calculating comprises calculating $VV_{ATP}$ as the greater of $T_{RL}$ and $T_{LR}$ minus the product of a predetermined factor and the lesser of $T_{RL}$ and $T_{LR}$.

8. The method of claim 1 wherein the instructing instructs the implantable device to deliver a pace to a site corresponding to the pace of the greater of $T_{RL}$ and $T_{LR}$, to wait for a time of $VV_{ATP}$ and then to deliver a pace to a site corresponding to the pace of the lesser of $T_{RL}$ and $T_{LR}$.

9. An implantable device comprising:
    one or more processors;
    memory; and
    control logic operational to
        deliver a pace using an electrode positioned on the lateral wall of the left ventricle of a heart,
        sense the pace using an electrode positioned in the right ventricle of the heart,
        determine a left to right directional conduction time ($T_{LR}$),
        deliver a pace using an electrode positioned in the right ventricle of the heart,
        sense the pace using an electrode positioned on the lateral wall of the left ventricle of the heart,
        determine a right to left directional conduction time ($T_{RL}$),
        calculate a site-to-site offset ($VV_{ATP}$) for multi-site anti-tachycardia pacing based on the left to right directional conduction time and the right to left directional conduction time; and
        deliver multi-site anti-tachycardia pacing using the site-to-site offset ($VV_{ATP}$).

10. The implantable device of claim 9 comprising control logic to deliver a pace to a site corresponding to the pace of the greater of $T_{RL}$ and $T_{LR}$, to wait for a time of $VV_{ATP}$ and then to deliver a pace to a site corresponding to the pace of the lesser of $T_{RL}$ and $T_{LR}$.

11. The implantable device of claim 9 comprising control logic to detect an arrhythmia and to call for anti-tachycardia pacing responsive to detection of an arrhythmia.

12. The implantable device of claim 11 further comprising one or more electrodes for sensing cardiac electrical activity and wherein the control logic to detect detects an arrhythmia by analyzing sensed cardiac electrical activity.

13. The implantable device of claim 9 comprising control logic to detect an arrhythmia, to detect ischemia and to call for multi-site anti-tachycardia pacing responsive to detection of ischemia and detection of an arrhythmia.

14. The implantable device of claim 13 wherein the arrhythmia comprises a ventricular tachycardia.

15. The implantable device of claim 14 wherein the ventricular tachycardia comprises a fast ventricular tachycardia according to a predetermined rate threshold.

16. An implantable device comprising:
one or more processors;
memory; and
control logic operational to
  detect an arrhythmia,
  detect ischemia,
  classify an arrhythmia as being a ventricular tachycardia,
  call for single site anti-arrhythmia therapy responsive to detection of an arrhythmia,
  call for multi-site anti-arrhythmia therapy responsive to detection of ischemia and a ventricular tachycardia, and
  deliver single or multi-site anti-arrhythmia therapy, wherein the multi-site anti-arrhythmia therapy comprises delivering a pace to one ventricle using a pacing site, waiting a site-to-site delay and then delivering a subsequent pace to the other ventricle using a different pacing site.

17. The implantable device of claim 16 wherein the multi-site anti-arrhythmia therapy comprises a site-to-site delay based at least in part on a directional conduction time along a direction and a directional conduction time along a different direction.

18. The implantable device of claim 16 wherein the site-to-site delay comprises a value based in part on a directional conduction time from the site to the different site and a directional conduction time from the different site to the site.

* * * * *